(12) United States Patent
Hart et al.

(10) Patent No.: US 11,602,886 B2
(45) Date of Patent: Mar. 14, 2023

(54) ADDITIVELY MANUFACTURED MESH MATERIALS, WEARABLE AND IMPLANTABLE DEVICES, AND SYSTEMS AND METHODS FOR MANUFACTURING THE SAME

(71) Applicant: Massachusetts Institute of Technology, Cambridge, MA (US)

(72) Inventors: Anastasios John Hart, Waban, MA (US); Sebastian William Pattinson, Cambridge (GB); Meghan Elizabeth Huber, Sunderland, MA (US); Jongwoo Lee, Cambridge, MA (US); Ricardo Roberts, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 391 days.

(21) Appl. No.: 16/773,313

(22) Filed: Jan. 27, 2020

(65) Prior Publication Data
US 2020/0238604 A1 Jul. 30, 2020

Related U.S. Application Data

(60) Provisional application No. 62/797,044, filed on Jan. 25, 2019.

(51) Int. Cl.
*B29C 64/118* (2017.01)
*A61F 2/00* (2006.01)
(Continued)

(52) U.S. Cl.
CPC .......... *B29C 64/118* (2017.08); *A61B 5/6802* (2013.01); *A61F 2/0063* (2013.01);
(Continued)

(58) Field of Classification Search
CPC ... B29C 64/118; A61B 5/6802; A61F 2/0063; A61F 5/0111; A61F 2240/001; B33Y 10/00; B33Y 80/00
See application file for complete search history.

(56) References Cited

U.S. PATENT DOCUMENTS

| 2008/0254263 A1 | 10/2008 | Yasui et al. |
| 2009/0068906 A1 | 3/2009 | Kawano et al. |

(Continued)

FOREIGN PATENT DOCUMENTS

WO 2013148719 A1 10/2013

OTHER PUBLICATIONS

International Search Report and Written Opinion for Application PCT/US2020/015192 dated May 14, 2020 (21 pages).
(Continued)

*Primary Examiner* — Brian Handville
(74) *Attorney, Agent, or Firm* — Barnes & Thornburg LLP

(57) ABSTRACT

Wearable and implantable devices that are used to support human anatomy and are formed using additive manufacturing are provided. Systems and methods for performing additive manufacturing allow for the formulation of a mesh material that has localized stiffness and slack in regions to best serve the needs of the patient. For example, regions of the mesh material can be designed to rigidly support portions of human anatomy, such as injured tissue, while regions of the mesh material adjacent to the injured tissue can be designed to closely mimic movement of the relevant human anatomy. For example, the mesh material can be formed in a manner such that it does not fold in those regions, and therefore is not obtrusive. The present disclosure allows for control of toolpaths when printing fibers used
(Continued)

to form the devices. Other devices, as well as systems and methods for creating the same, are also provided.

22 Claims, 13 Drawing Sheets

(51) Int. Cl.
| | |
|---|---|
| *A61B 5/00* | (2006.01) |
| *A61F 5/01* | (2006.01) |
| *B33Y 80/00* | (2015.01) |
| *B33Y 10/00* | (2015.01) |

(52) U.S. Cl.
CPC .............. *A61F 5/0111* (2013.01); *B33Y 10/00* (2014.12); *B33Y 80/00* (2014.12)

(56) References Cited

U.S. PATENT DOCUMENTS

| | | |
|---|---|---|
| 2015/0223928 A1 | 8/2015 | Limem et al. |
| 2016/0021948 A1 | 1/2016 | MacNeil |
| 2016/0054185 A1 | 2/2016 | Servati et al. |
| 2016/0262208 A1 | 9/2016 | Hsieh |
| 2017/0165908 A1 | 6/2017 | Pattinson et al. |
| 2018/0158372 A1* | 6/2018 | Wang ..................... G09B 23/30 |

OTHER PUBLICATIONS

Akbari, M. et al.; Textile Technologies and Tissue Engineering: A Path Toward Organ Weaving; Adv. Healthc. Mater.; Apr. 2016.
Alderman, A. K. et al.; Financial Impact of Breast Reconstruction in Academic Practice; Plast. Reconstr. Surg.; 2010; 123, 1408-1413.
Bettini, P.; Alitta, G.; Sala, G.; Di Landro, L. Fused Deposition Technique for Continuous Fiber Reinforced Thermoplastic. J. Mater. Eng. Perform. 2017, 26, 843-848.
Bickel, B.; Moritz, B.; Otaduy, M. A.; Lee, H. R.; Matusik, W. Design and Fabrication of Materials with Desired Deformation Behavior. 2009.
Bingham, G. A.; Hague, R. Efficient Three Dimensional Modelling of Additive Manufactured Textiles. 2013, 4, 269-281.
Calvo, B.; Ramirez, A.; Alonso, A.; Grasa, J.; Soteras, F.; Osta, R.; Mu??oz, M. J. Passive Nonlinear Elastic Behaviour of Skeletal Muscle: Experimental Results and Model Formulation. J. Biomech. 2010, 43, 318-325.
Chao, A. H.; Khansa, I.; Kaiser, C.; Bell, J.; Miller, M. J. The Differential Impact of Plastic Surgery Subspecialties on the Financial Performance of an Academic Clinical Practice. Plast. Reconstr. Surg. 2014, 133, 748e-755e.
Choi, S.; Park, J.; Hyun, W.; Kim, J.; Kim, J.; Lee, Y. B.; Song, C.; Hwang, H. J.; Kim, J. H.; Hyeon, T.; et al. Stretchable Heater Using Ligand-Exchanged Silver Nanowire Nanocomposite for Wearable Articular Thermotherapy. ACS Nano 2015, 9, 6626-6633.
Clausen, A.; Wang, F.; Jensen, J. S.; Sigmund, O.; Lewis, J. A. Topology Optimized Architectures with Programmable Poisson's Ratio over Large Deformations Supporting Info. Adv. Mater. 2015, 27, 5523-5527.
De Bruijn, H. P.; Johannes, S. Mastopexy with 3D Preshaped Mesh for Long-Term Results: Development of the Internal Bra System. Aesthetic Plast. Surg. 2008, 32, 757-765.
Dreifus, G.; Goodrick, K.; Giles, S.; Patel, M.; Foster, R. M.; Williams, C.; Lindahl, J.; Post, B.; Roschli, A.; Love, L.; et al. Path Optimization Along Lattices in Additive Manufacturing Using the Chinese Postman Problem. 3D Print. Addit. Manuf. 2017, 4, 98-104.
Eils, E.; Demming, C.; Kollmeier, G.; Thorwesten, L.; Völker, K.; Rosenbaum, D. Comprehensive Testing of 10 Different Ankle Braces: Evaluation of Passive and Rapidly Induced Stability in Subjects with Chronic Ankle Instability. Clin. Biomech. 2002, 17, 526-535.
Gladman, A. S.; Matsumoto, E. A.; Nuzzo, R. G.; Mahadevan, L.; Lewis, J. A. Biomimetic 4D Printing. Nat. Mater. 2016, 1-7.
He, Y.; Xue, G.; Fu, J. Fabrication of Low Cost Soft Tissue Prostheses with the Desktop 3D Printer. Sci. Rep. 2015, 4, 6937.
Janssen, K. W.; Hendriks, M. R. C.; Van Mechelen, W.; Verhagen, E. The Cost-Effectiveness of Measures to Prevent Recurrent Ankle Sprains: Results of a 3-Arm Randomized Controlled Trial. Am. J. Sports Med. 2014, 42, 1534-1541.
Johnson, A.; Bingham, G. A.; Wimpenny, D. I. Additive Manufactured Textiles for High-Performance Stab Resistant Applications. Rapid Prototyp. J. 2013, 19, 199-207.
Kingsnorth, A.; LeBlanc, K. Hernias: Inguinal and Incisional. Lancet 2003, 362, 1561-1571.
Klosterhalfen, B.; Junge, K.; Klinge, U. The Lightweight and Large Porous Mesh Concept for Hernia Repair. Expert Rev. Med. Devices 2005, 2, 103-117.
Levin, L. S. The Business of Academic Plastic Surgery. Plast. Reconstr. Surg. 2010, 303-307.
Lussenburg, K.; Velden, N. Van Der; Doubrovski, Z.; Geraedts, J.; Karana, E. Designing with 3D Printed Textiles. In Proceedings of the 5th International Conference on Additive Technologies; 2003; pp. 74-81.
Matsuzaki, R.; Ueda, M.; Namiki, M.; Jeong, T.-K.; Asahara, H.; Horiguchi, K.; Nakamura, T.; Todoroki, A.; Hirano, Y. Three-Dimensional Printing of Continuous-Fiber Composites by in-Nozzle Impregnation. Sci. Rep. 2016, 6, 23058.
Mccann, J.; Mankoff, J.; Hodgins, J. A Compiler for 3D Machine Knitting. 2011, 35, 1-11.
McGuine, T. A.; Brooks, A.; Hetzel, S. The Effect of Lace-up Ankle Braces on Injury Rates in High School Basketball Players. Am. J. Sports Med. 2011.
Patra, S.; Young, V. A Review of 3D Printing Techniques and the Future in Biofabrication of Bioprinted Tissue. Cell Biochem. Biophys. 2016, 74, 93-98.
Peng, H.; Mankoff, J.; Hudson, S. E.; Mccann, J. A-Layered-Fabric-3D-Printer-for-Soft-Interactive-Objects-Paper. 2015.
Pott, P. P.; Schwarz, M. L. R.; Gundling, R.; Nowak, K.; Hohenberger, P.; Roessner, E. D. Mechanical Properties of Mesh Materials Used for Hernia Repair and Soft Tissue Augmentation. PLoS One 2012, 7, 1-10.
Qin, Z.; Compton, B. G.; Lewis, J. A.; Buehler, M. J. Structural Optimization of 3D-Printed Synthetic Spider Webs for High Strength. Nat. Commun. 2015, 6, 1-7.
Rao, V. K.; Schmid, D. B.; Hanson, S. E.; Bentz, M. L. Establishing a Multidisciplinary Academic Cosmetic Center. Plast. Reconstr. Surg. 2011, 128, 741e-6e.
Resnick, A. S.; Corrigan, D.; Mullen, J. L.; Kaiser, L. R. Surgeon Contribution to Hospital Bottom Line. Trans. . . . Meet. Am. Surg. Assoc. 2005, 123, 224-233.
Siegler, S.; Marchetto, P.; Murphy, D. J.; Gadikota, H. R. A Composite Athletic Tape With Hyperelastic Material Properties Improves and Maintains Ankle Support During Exercise. J. Orthop. Sport. Phys. Ther. 2011, 41, 961-968.
Tamura, K.; Radzak, K. N.; Vogelpohl, R. E.; Wisthoff, B. A.; Oba, Y.; Hetzler, R. K.; Stickley, C. D. The Effects of Ankle Braces and Taping on Lower Extremity Running Kinematics and Energy Expenditure in Healthy, Non-Injured Adults. Gait Posture 2017, 58, 108-114.
Trombetta, R.; Inzana, J. A.; Schwarz, E. M.; Kates, S. L.; Awad, H. A. 3D Printing of Calcium Phosphate Ceramics for Bone Tissue Engineering and Drug Delivery. Ann. Biomed. Eng. 2017, 45, 23-44.
Wang, T. Y.; Nelson, J. a.; Corrigan, D.; Commack, T.; Serletti, J. M. Contribution of Plastic Surgery to a Health Care System. Plast. Reconstr. Surg. 2012, 129, 154e-160e.
White, J.; Foley, M.; Rowley, A. A Novel Approach to 3D-Printed Fabrics and Garments. 3D Print. Addit. Manuf. 2015, 2, 145-149.
Wu, E. Improving the Longevity and Results of Mastopexy and Breast Reduction Procedures: Reconstructing an Internal Breast Support System with Biocompatible Mesh to Replace the Supporting Function of the Ligamentous Suspension. Aesthetic Plast. Surg. 2011.

\* cited by examiner

ADDITIVELY MANUFACTURED MESH MATERIALS, WEARABLE AND IMPLANTABLE DEVICES, AND SYSTEMS AND METHODS FOR MANUFACTURING THE SAME

CROSS REFERENCE TO RELATED APPLICATION

This application claims priority to and the benefit of U.S. Provisional Application No. 62/797,044, filed Jan. 25, 2019, and titled "Additively Manufactured Mesh Materials, Wearable and Implantable Devices, and Systems and Methods for Manufacturing the Same," which is a continuation-in-part of U.S. Patent Application Publication No. 2017/0165908, entitled "Systems, Devices, and Methods for Deposition-Based Three-Dimensional Printing," filed Dec. 12, 2016, each of which is incorporated by reference herein in its entirety.

GOVERNMENT RIGHTS

This invention was made with Government support under Grant No. SMA-1415129, CMMI-1346638, and BCS-1724135 awarded by the National Science Foundation. The Government has certain rights in the invention.

FIELD

The present disclosure relates to materials, and typically mesh materials, that have been produced by way of additive manufacturing techniques to assist with the treatment and/or prevention of soft tissue injuries. As described, the materials include various types of wearable devices, such as ankle braces and other types of devices that can be worn on body parts (e.g., wrists, knees, etc.), and are manufactured to provide controllable local stiffness at desired locations of the wearable device. System, devices, and methods for manufacturing such materials, wearable devices, etc. are also provided.

BACKGROUND

Human bodies come in many shapes and sizes, and devices that are intended to be implanted into or worn on the body tend to function better if they are customized to those shapes and sizes. Additive manufacturing (AM) enables the production of parts that are both individually customized and geometrically complex. AM is therefore ideally suited to enhancing devices that must fit onto or into people by better mimicking the complexity and diversity of the body. These advantages have already led to numerous additively manufactured medical devices, such as orthodontics, bone replacements, and prostheses. That these devices all interface with hard tissues reflects the greater ease, in terms of hardware and software, of printing hard materials with high density. Soft tissues (including muscle, nerves, fat, and ligaments), however, also often require mechanical support to prevent or heal injury. Ankle sprains due to excessive ankle inversion are the most prevalent acute musculoskeletal injury during physical activity, with approximately 2 million sprains occurring every year in the United States alone. Prominent examples of devices used to prevent or heal soft tissue injuries include surgical meshes, which are used to mechanically support soft tissue as it heals following surgery, and braces, which restrict movement (for example of the ankle) to prevent injury.

Externally worn devices are often used to immobilize joints including wrists, ankles, and shoulders after injury while healing proceeds. These devices are typically made from stiff, woven textiles such as nylon or polyesters and feature Velcro straps to tighten the brace to the joint. During the early stages of recovery from severe injuries, such as full tendon or ligament tears, even more stiff polymer or metal braces may be worn to increase the degree of immobilization of the joint. With regard to ankle braces in particular, there are three main categories: soft, semi-rigid, and rigid. The difference among these braces is the degree of stiffness (or "stabilization") that they add to the ankle joint. Soft and semi-rigid braces are often intended for prophylactic use during sports to prevent recurrent ankle injuries after a mild/moderate ankle sprain. Rigid braces are typically used immediately after a severe ankle sprain or for severe chronic ankle instability (CAI).

There are several challenges with braces, however, ankle or otherwise. For example, because braces are heavy and uncomfortably restrict most or all of the degrees of freedom of a joint, they are rarely worn preventatively; they are often too cumbersome. Additionally, braces (e.g., ankle braces) can restrict virtually all degrees of freedom of the associated body part (e.g., ankle), thus leading to muscle atrophy and making the user more susceptible to future injury. Still further, the immobilization of one body part can often place excessive forces on another body part. For example, the immobilization of the ankle can lead to excessive forces being placed on the knee joint, often causing people who have suffered ankle injuries to experience subsequent knee problems. Further, the mechanical mismatch between wearers'/patients' tissues and the device can lead to significant complications, such as hernia recurrence due to migration of the mesh away from the hernia site.

Soft tissue devices such as these could significantly benefit from the customization and complex geometries enabled by additive techniques. For example, an ankle brace that can prevent motions that will lead to injury while leaving the ankle otherwise free to move naturally would be preferable. A mesh that could be individually tailored to fit a wearer in terms of both mechanics and geometry could potentially reduce complications that result from mechanical mismatches between tissues being treated, or near the location being treated, and the device being used for treatment. Producing devices that match soft tissue mechanics is very challenging partly because tissues such as muscle, tendons, and ligaments often feature non-linear tensile stress-strain responses, with an initially low stiffness that rapidly increases as the tissue becomes taut. The mechanical response also varies greatly in different directions, between different tissue types, and also between different patients.

Existing methods to produce soft-tissue devices typically use conventional fabrics made by knitting or weaving. To the extent there have been developments in designing conventional fabrics, such processes do not offer a sufficient deal of local control over fabric mechanics to accurately mimic tissue. To date, AM techniques for producing various wearable and implantables result in devices that are not very strong and durable because AM fabrics are much weaker and more brittle than conventional fabrics, and that it is therefore difficult to produce thin filamentary geometries used to achieve flexibility (or "drape") in conventional textiles because the fibers would break. Moreover, the high bending strains caused by the fact that the parts are unable to slide relative to one another also limit AM fabrics' flexibility. AM fabrics have therefore tended to produce chainmail-like designs made by selective laser sintering or stereolithography that are too bulky and brittle to be comfortably worn, let alone implanted, and also make it difficult to locally control their properties. To the extent direct write-based processes can be used to produce the types of materials desired, such use is complicated by requiring more sophisticated toolpath planning than conventional planar layer-by-layer toolpath software, which typically simply uses infill patterns from computer numerical control (CNC) machining such as raster, zigzag, contour, and spiral. Such infill patterns are not typically suitable for fabrics, do not enable local control of mechanics, and produce many discontinuities in the extrusion that weaken the part.

Accordingly, there is a need for a device that mechanically matches a patient/wearer that features locally varying, anisotropic, and non-linear tensile mechanical response, while also being porous enough to enable tissue integration (in the case of an implant) or breathability (in the case of an external device), as well as systems and methods for manufacturing the same.

SUMMARY

The present disclosure provides for systems and methods to additively manufacture mesh with controllable local stiffness. The provided systems and methods can enable (1) optimized mechanics that cannot be achieved by conventional textiles, and (2) customization of 3D mesh geometry and mechanics to patient anatomy, thereby providing the resulting device (e.g., wearable, implantable) unique potential to reduce complications and enhance comfort, movement, and aesthetic outcome in ankle and other soft tissue injuries.

More particularly, the present disclosure provides for direct-write processes that enable explicit control of a toolpath and hardware that allows patterning of continuous fibers to lead to control over local fabric geometry, topology, and composition, and thereby local and anisotropic nonlinear mechanical response. The direct-write process can be carried out by software implementations that communicate with an AM printer. The focus of the present disclosure provides for specific application of the direct-write processes to manufacture mesh materials and wearable devices, such as an ankle brace. Many other devices are provided for by, or are derivable from, the present disclosures, including but not limited to other types of braces (e.g., knee brace, wrist brace, back brace, neck brace), adhesive tapes (e.g., athletic tape), and implantable devices (e.g., hernia mesh).

In one exemplary embodiment, a wearable or implantable device includes a mesh material that is configured to conform to a portion of an anatomy to serve as a support. The mesh material is made from one or more fibers, and has a plurality of unit cells. Each unit cell of the plurality of unit cells includes at least one portion of fiber from the one or more fibers passing through the unit cell. The at least one portion of fiber that passes through the unit cell include at least one wave formed in that portion. The at least one wave is configured to influence a stiffness of the unit cell upon at least one of bending or stretching.

In some embodiments, the at least one portion of fiber from the one or more fibers passing through the unit cell can include at least two portions of fiber from the one or more fibers passing through the unit cell. A first portion of the at least two portions of fiber can intersect and can be disposed at an angle with respect to a second portion of the at least two portions of fiber. At least one of the first portion or the second portion of the at least two portions of fiber that pass through the unit cell can have the at least one wave formed therein.

The device can be a wearable device, and the mesh material that is configured to conform to a portion of an anatomy to serve as a support can serve as a mechanical support device (e.g., a brace). In some such embodiments, the wearable device can be ankle brace, a knee brace, a wrist brace, a back brace, a neck brace, of another type of brace. For example, the brace can be an ankle brace that is predominantly made from the mesh material. In some instances in which the brace is an ankle brace, the ankle brace can be a pre-existing ankle brace, with the mesh material being an additional material that is associated with the pre-existing ankle brace. In some other embodiments, the device can be an implantable device. For example, the implantable device can include a hernia mesh. In some embodiments, the mesh material is non-woven. The mesh material can be manufactured, for example, by extrusion of thermoplastic from one or more nozzles.

The device can be additively manufactured by extrusion of a mesh onto at least one of a: fabric, frame, support structure, adhesive tape, or human. The fabric, frame, support structure, adhesive tape, and/or human can be at least one the: fabric, frame, or support structure is configured to be worn by a human. In some such embodiments, the fabric, frame, and/or support structure is configured to be worn on a hand of the human.

The first portion of the at least two portions of fiber can be disposed substantially orthogonally with respect to the second portion of the at least two portions of fiber. In some such embodiments, each unit cell of the plurality of unit cells can include: (1) the first portion of the at least two portions of fiber; (2) the second portion of the at least two portions of fiber; (3) a third portion of the at least two portion of fiber; and (4) a fourth portion of the at least two portions of fiber, with the first and third portions being disposed substantially orthogonally with respect to the second and fourth portions. The first, second, third, and fourth portions of fiber can each be from separate fibers, which can be a first fiber, a second fiber, a third fiber, and a fourth fiber, respectively. A region of the mesh material can include localized slack.

The first portion of the at least two portions of fiber and the second portion of the at least two portions of fiber can be comprised of different materials. In some embodiments, the one or more fibers can comprise at least one continuous fiber. The at least one continuous fiber can be continuous across multiple unit cells of the plurality of unit cells. In some such instances, the at least one continuous fiber can be continuous across an entire length of the mesh material. In some embodiments in which there is at least one continuous fiber, the at least one continuous fiber is a single continuous fiber that makes up the entirety of the one or more fibers such that the one continuous fiber forms the mesh material.

The first portion and the second portion of the at least two portions of fiber in some unit cells of the plurality of unit cells can be selectively adhered together. Further, the first portion and the second portion of the at least two portions of fiber in some other unit cells of the plurality of unit cells can be selectively not adhered. In some embodiments in which there is selective adhering, the first and second portions of the at least two portions of fibers that are selectively adhered together can be non-stochastically and rationally distributed with respect to a volume of the mesh material.

A region of the mesh material can include a portion where a Poisson's ratio is negative, thereby allowing the mesh material to curve around a portion of anatomy when stretched without folding. Alternatively, or additionally, the mesh material can include a portion having a curvature formed in it, the mesh material having a non-linear tensile response at a location of the curvature. The mesh material can have a highly non-linear stiffness such that a modulus is low under low strain conditions and the modulus is high under high strain conditions.

In some embodiments, at least one fiber of the one or more fibers can include a conductive thread that is configured to apply heat to a portion of an anatomy with which the mesh material is associated. Alternatively, or additionally, at least one fiber of the one or more fibers can include a conductive material that is configured to operate as a strain sensor. In some embodiments at least one fiber of the one or more fibers can include a pre-made fiber.

In another exemplary embodiment of a wearable or implantable device, the device includes both a first region and a second region. The first region has a plurality of first portions of extruded fiber that are disposed in it, with the plurality of first portions of extruded fiber being configured to attach to a portion of human anatomy in a desired location. The second region has a plurality of second portions of extruded fiber disposed in it, with the plurality of second portions of extruded fiber being configured to conform to a portion of the human anatomy adjacent to the portion of the device attached to a portion of human anatomy in a desired location such that the plurality of second portions of extruded fiber permit substantially typical movement for the portion of the human anatomy adjacent they conform to unless that anatomy moves in a direction to an extent that would cause it to become injured. At least one of local fabric geometry, topology, or composition of extruded fiber controls whether portions of extruded fiber are the plurality of first portions or the plurality of second portions of the extruded fiber.

The extruded fiber can form a mesh material. The mesh material, in some instances, can be non-woven. In some instances, the mesh material can be manufactured by extrusion of thermoplastic from one or more nozzles. In at least embodiments in which the extruded fiber forms a mesh material, the extruded fiber can include at least one continuous fiber. The at least one continuous fiber can be continuous across an entire length of the mesh material. Alternatively, or additionally, the at least one continuous fiber can be a single continuous fiber that makes up the entirety of the extruded fiber such that the one continuous fiber forms the mesh material. In embodiments in which the fiber forms a mesh material, the mesh material can include a portion that has a curvature formed in it, with the mesh material having a non-linear tensile response at a location of the curvature. Alternatively, or additionally, the mesh material can have a highly non-linear stiffness such that a modulus is low under strain conditions and the modulus is high under high strain conditions.

The second region can include localized slack. Portions of the extruded fiber can be selectively bonded together, while other portions of the extruded fiber can be selectively unbonded. In some such embodiments, the portions of the extruded fiber that can be selectively bonded together can be non-stochastically and rationally distributed with respect to a volume of the device. In some embodiments, at least a portion of at least one of the first region or the second region has a Poisson's ratio that is negative, thereby allowing the portion of that region to curve around a portion of an anatomy when stretched without folding.

The device can be additively manufactured by extrusion of a mesh onto at least one of a: fabric, frame, support structure, or human. The fabric, frame, support structure, and/or human can be at least one the: fabric, frame, or support structure is configured to be worn by a human. In some such embodiments, the fabric, frame, and/or support structure is configured to be worn on a hand of the human.

The device can be a wearable device, such as a brace. Some non-limiting examples of such braces include an ankle brace, a knee brace, a wrist brace, a back brace, and a neck brace. In some instances in which the brace is the ankle brace, the ankle brace is predominantly made from the extruded fiber, and the extruded fiber forms a mesh material. In some other instances in which the brace is the ankle brace, the brace can include a pre-existing ankle brace, with the extruded fiber being additional material that is associated with the pre-existing ankle brace. In some other embodiments, the device can be an implantable device, such as a hernia mesh or surgical mesh. In some other embodiments, the device can include an adhesive tape, such as an adhesive athletic tape.

In some embodiments, the device can include a conductive thread that is configured to apply heat to a portion of an anatomy with which the extruded fiber is associated. Alternatively, or additionally, the extruded fiber can include a conductive material that is configured to operate as a strain sensor. In some embodiments the extruded fiber can include a pre-made fiber.

One exemplary method for manufacturing a mesh material for medical support includes depositing a first portion of fiber onto a surface, depositing a second portion of fiber onto at least one of the first portion of fiber and the surface, and controlling at least one of local fabric geometry, topology, or composition of the deposited fiber to create portions that are configured to attach to a portion of human anatomy in a desired location and portions that are configured to conform to a portion of the human anatomy such that such portions permit substantially typical movement for a desired portion of the human anatomy unless that portion moves in a direction and to an extent that it would cause it to become injured. The second portion includes at least one wave formed in it to allow the second portion to bend with a lower stiffness before it stretches.

The surface can be an adhesive substrate, and at least one of depositing a first portion of fiber or depositing a second portion of fiber can include using the adhesive substrate to passively pull the respective first or second portion out of a nozzle and onto the adhesive substrate or the first portion of fiber. In some such embodiments, the method can further include depositing a third portion of fiber onto the adhesive substrate to change a direction in which the fiber is being printed.

In some embodiments, the surface can include a first thermoplastic layer, and the method can include depositing a second thermoplastic layer on top of the first and second portions of fiber to sandwich the first and second portions of fiber between the first and second thermoplastic layers.

The medical support can include a mechanical support device (e.g., brace). The mechanical support device can be configured to support one of: an ankle, a knee, a wrist, a back, or a neck. In other embodiments the medical support can include an implantable device, such as a hernia mesh. In still other embodiments the medical support can include an adhesive tape, such as an adhesive athletic tape.

The mesh material can be non-woven. In some embodiments, the first portion of fiber and the second portion of fiber can form at least one continuous fiber. The one continuous fiber(s) can be continuous across an entire length of the mesh material in some instances. The one continuous fiber(s) can be a single continuous fiber that forms the entirety of the mesh material. In some embodiments, the fiber can include a pre-made fiber.

Depositing a second portion of fiber can result in a region of the mesh material comprising localized slack. In some embodiments, the method can include selectively binding together portions of the first portion of the fiber and portions of the second portion of fiber, and selectively leaving portions of the first portion of the fiber and portions of the second portion of fiber unbonded. In some such embodiments, at least some of the portions of the first portion of the fiber and the portions of the second portion of the fiber that are selectively bonded together can be non-stochastically and rationally distributed with respect to a volume of the mesh material. The method can include forming a region of the mesh material in which a Poisson's ratio is negative, thereby allowing the mesh material to curve around a portion of an anatomy without folding. In some embodiments, the method can include forming a portion of the mesh material to have a curvature formed in it, with the mesh material having a non-linear tensile response at a location of the curvature. The fiber can be attached to at least one of a: sock, shoe, or other wearable product.

BRIEF DESCRIPTION OF THE DRAWINGS

This disclosure will be more fully understood from the following detailed description taken in conjunction with the accompanying drawings, in which.

DETAILED DESCRIPTION

Figure 1A:
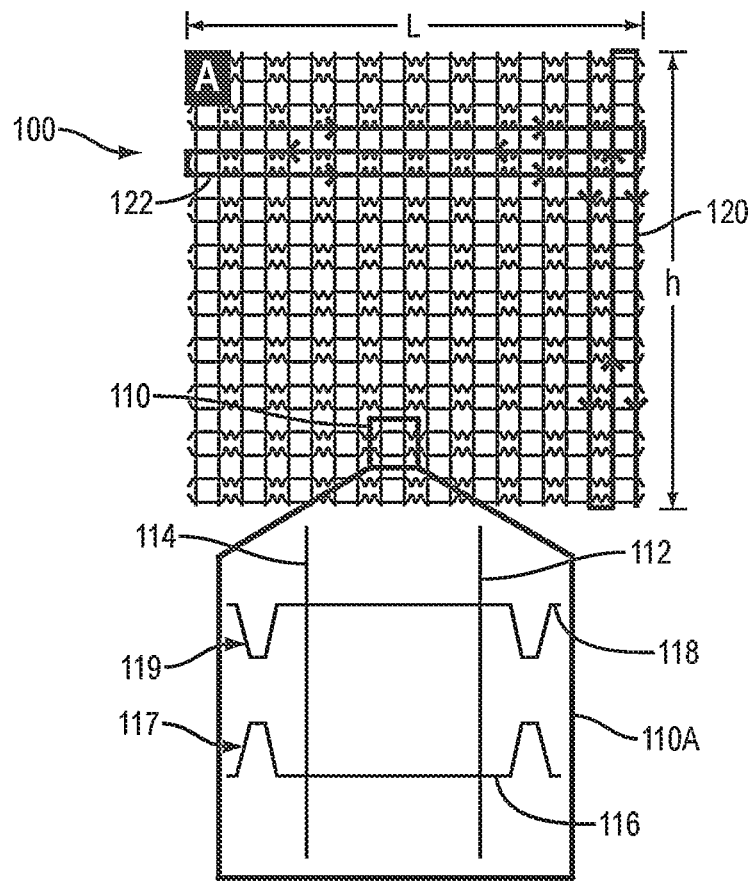
FIG. 1A is a top view of one exemplary embodiment of a schematic illustration of a mesh comprised of a plurality of unit cells in accordance with the present disclosure.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Various wearable and implantable materials, such as braces and other immobilization devices, are either provided for herein or are easily derivable in view of the present disclosures. The materials and devices disclosed often include mesh materials, and are configured to provide localized slack such that the materials and devices can provide the necessary and/or desirable support at certain locations of a patient's body, while not unduly restricting other locations near the area of treatment. One non-limiting example of devices disclosed herein is an ankle brace that provides support at the location of the local injury, whether for preventive or healing purposes, while still allowing for other portions of the nearby anatomy to move essentially normally. Methods for producing an ankle brace of this nature, and other wearable and implantable devices (also referred to herein as wearable and implantables), including, for example, implantable mesh (e.g., hernia mesh), garments, braces, and adhesive tape (e.g., athletic tape), are disclosed, as are systems that can be operated to produce such braces and devices. A person skilled in the art will both understand what wearables and implantables are, and will understand a variety of wearables and implantables that can be produced in view of the present disclosures.

The present disclosure provides for a hierarchical approach to designing a fabric structure with locally varying properties. More particularly, a full fabric can be divided into a plurality of unit cells, which can, in turn, be composed of one or more element made up of one or more fiber. A composition, design, and manufacture of the unit cells can produce diverse aggregate mechanical responses in the fabric that can be locally controlled and varied. As used herein, a mechanical response can refer to the response of the fabric vis-à-vis the plurality of unit cells to application of a tensile force. The mechanical response can include, for example, strain, stress, and stiffness properties of the fabric. Integration of adjacent unit cells into fabrics or meshes can form larger scale functional units that can have a known and controlled mechanical response. A unit cell can be designed such that its mechanical response to a force can be determined in a predictable way based, at least in part, on the elements of the unit cell. For example, the unit cell can be designed such that the most flexible part of the unit cell can be along a direction of loading. In some embodiments, a mesh can be designed to include a section with built-in slack that can be configured to deform along a direction of loading.

A unit cell can be composed of one or more elements. In one embodiment, a unit cell can include four fiber portions (sometimes referred to as "elements"), two of which can pass through the unit cell in a horizontal orientation, and two that can pass through the unit cell in a vertical orientation. The two fiber portions that pass through the unit cell in the horizontal orientation can extend orthogonally relative to the two fiber portions that pass through the unit cell in the vertical orientation. In some instances, an element of a unit cell can include one or more adjacent fiber portions that can be bonded together. A boundary condition can be enforced such that the element can be continuous between unit cells, which can allow for a continuous toolpath, and therefore fiber, along a whole length of the full fabric or mesh. One or more of the elements of the unit cell can include a wave-feature, described in detail below, which can contribute to a non-linear mechanical response of the element. Meshes with configurations and constructions as disclosed herein can improve fabric strength and can allow for the incorporation of a broader range of materials, such as pre-made fibers, into the mesh.

Fabrication and Composition of Meshes

FIG. 1A shows a schematic illustration of one embodiment of a mesh 100 fabricated in accordance with the present disclosure. The mesh 100 can have a length L and a height h that can represent the full mesh or fabric. The mesh 100 can include a plurality of unit cells 110. Inlay 110A shows one such unit cell 110 in greater detail. More particularly, in one embodiment, the unit cell 110 can include an element with four fiber portions—112, 114, 116, and 118—extending therethrough. Fibers 112 and 114 can extend through the unit cell 110 in a vertical or substantially vertical orientation (i.e., along an axis parallel or substantially parallel to the height H of the mesh 100). Fibers 116 and 118 can extend through the unit cell in a horizontal or substantially horizontal orientation (i.e., along an axis parallel or substantially parallel to the length L of the mesh 100). In some embodiments, the fiber portions 112, 114 can extend substantially orthogonally relative to the fiber portions 116, 118.

As discussed in detail below, the construction and configuration of the fibers 112, 114, 116, and 118 (i.e., the element of the unit cell 110) can be manufactured such that mechanical properties of the mesh 100 can be locally controlled. The mesh 100 can be printed with an extruder or other tool that can print or otherwise extrude or lay down fiber. In this manner, the mesh 100 can be a non-woven mesh. Exemplary portions of a toolpath 120, 122 can be seen in FIG. 1A along with arrows indicating a direction of movement of the tool. In some embodiments, one or more pre-made fibers can also be included in the mesh 100. As used herein, the term pre-made fiber can refer to a fiber that is not extruded during a printing process used to make the mesh or device into which the mesh can be incorporated. In contrast, an extruded fiber, as used herein, can refer to a fiber that is extruded during the printing process of the mesh or device.

At least one fiber portion 112, 114, 116, 118 extending through the unit cell 110 can exhibit a non-linear tensile response. In some embodiments, a curvature can be introduced into a pattern of the printed mesh 100, which can provide for the non-linear tensile response. For example, one or more of the fibers 112, 114, 116, and 118 can include a curvature in the form of a wave, such as a wave 117 in the fiber 116 and/or wave 119 in the fiber 118. Under a tensile force, the wave(s) of these fibers 116, 118 can straighten prior to a response dominated by a stretching of the fiber itself. Once straightened, the fibers 116, 118 can exhibit a tensile response with predominately fiber-stretching characteristics. A stiffness of the fiber 116, 118 during straightening (i.e., bending) of the waves 117, 119 can be lower than a stiffness of the fiber during stretching. This variation in stiffness during the bending-phase and the stretching-phase can lead to a non-linear mechanical response of the fiber 116, 118 to a tensile force. As discussed in detail below, a strain of the fiber 116, 118 at which a transition from low-stiffness (i.e., the bending phase) to high stiffness (i.e., the stretching phase) can be controlled, at least in part, through a height or amplitude of the wave feature 117, 119. Moreover, one or more pre-made fibers having a low bending but high stretching stiffness can be introduced into one or more unit cells 110 of the mesh 100 such that greater stiffness gradients can be created across the mesh.

In some embodiments, the non-linear mechanical response of an element, unit cell, and/or region of a mesh can be controlled by varying one or more properties described herein such that the mesh has a mechanical response intended for a particular application. For example, a mesh can be configured to provide added stiffness or support to a portion of the anatomy of a user/wearer when motion in a first direction increases beyond a desired range, while allowing unimpeded motion in one or more other directions. In this manner, the mesh can prevent injury from undesired motion in the first direction without impeding motion in other directions. In some embodiments, a mesh of the present disclosure can be designed to be implanted within the body. A mechanical response of a particular element, unit cell, and/or region of the mesh can be controlled and designed to have a stiffness that can match a stiffness of soft tissue, and, more particularly, of healthy tissue that can surround the mesh once implanted. This is challenging because often soft tissue features high local variation in mechanics, non-linear mechanics, and also high degrees of anisotropy. Matching the mechanics of the mesh to be implanted to about the same mechanics of surrounding healthy tissue, or through its interaction with surrounding tissue, lead to similar overall mechanics as would be expected from healthy tissue. This can lead to healthier tissue ingrowth, and also can potentially reduce complications, such as chronic pain.

Figure 1B:
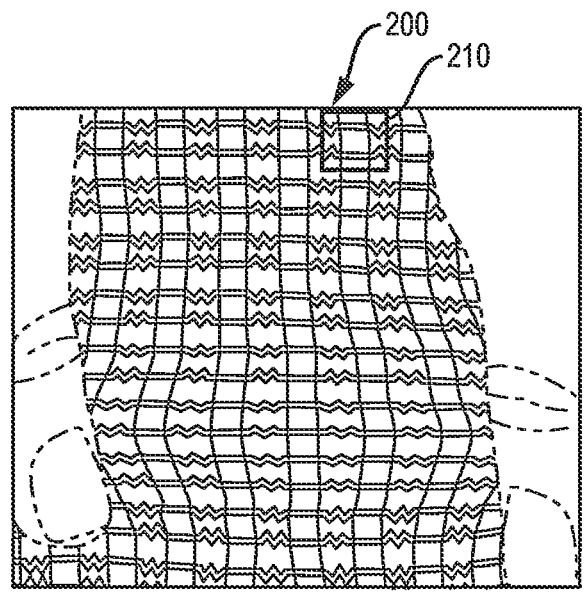
FIG. 1B is a top view of another exemplary embodiment of a mesh with a tensile force applied thereto.

FIG. 1B is a mesh 200 fabricated in accordance with the present disclosure with a tensile force applied thereto, in this instance by way of a human subject applying the tensile force with hands. Similar to the mesh 100 of FIG. 1A, the mesh 200 can be composed of a plurality of unit cells 210. As illustrated in FIGS. 1A and 1B, there can be an overlap between a fiber extending in the vertical orientation and a fiber extending in the horizontal orientation. This overlap can result in a cohesive mesh or fabric. For medical applications, this can be useful to prevent tissue from straining beyond a point at which injury can occur.

Figure 1C:
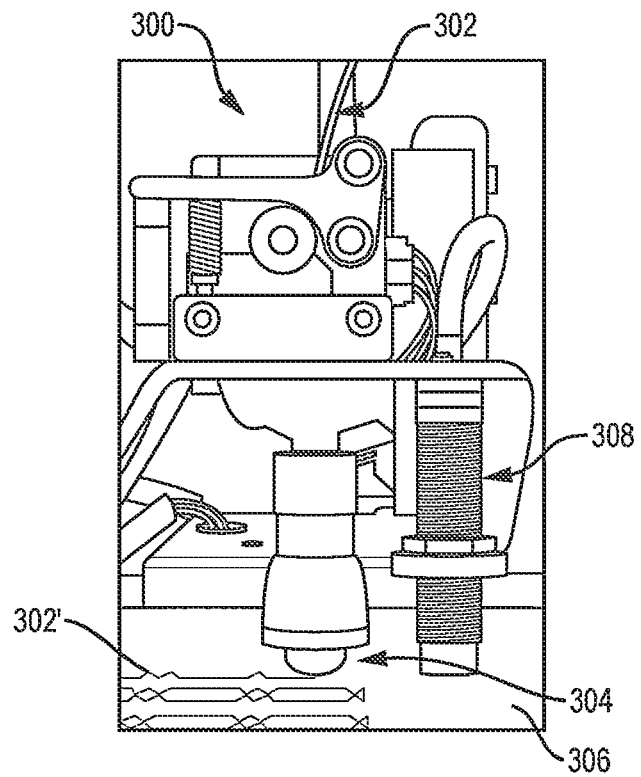
FIG. 1C is a front view of one exemplary embodiment of an extruder that can be used to print a mesh.

While a number of different systems can be used, or adapted for use, to form the filaments or fibers to creates meshes and other similar devices as provided for herein, one non-limiting example of such a system is an extruder 300, as illustrated in FIG. 1C. The extruder 300 can be used for printing a mesh, such as, for example, the mesh 200 of FIG. 1B. More particularly, a filament 302 can be fed into the extruder 300 and can be deposited from a nozzle 304 onto a substrate 306 as an extruded fiber 302'. In some embodiments, the extruder 300 can include a sensor 308 that can sense a distance between a distal end of the nozzle 304 and a proximal-facing surface of the substrate 306. As discussed in detail below, the distance between the substrate 306 and the nozzle 304, also referred to as a z-height of the nozzle 304, can impact qualities of the mesh printed by the extruder 300. A person skilled in the art will appreciate other features of an extruder or printer as illustrated by the extruder 300 but not described herein. Likewise, a person skilled in the art will appreciate other features of an extruder that can be incorporated into those capable of fabricating the meshes, devices, and the like provided for herein and/or performing the printing methods provided for herein, as well as other types of extruders and printers with which the present disclosures can be used. Accordingly, a description of such features and other printing systems or devices is unnecessary.

In some embodiments, one or more element of a unit cell can be a fiber portion of a continuous fibers. A continuous fiber can be a fiber that can extend across multiple unit cells of a mesh or fabric, and, in some instances, can extend across an entire length of the mesh or fabric. In some embodiments, a single continuous fiber can make up an entirety of the fibers of the mesh or fabric. In other words, a mesh or a fabric can be formed from a single continuous fiber. Incorporating continuous fiber into unit cells of a mesh can require design adaptations. For example, when laying down a continuous fiber, the continuous fiber may not be able to easily change direction. Accordingly, in some embodiments, the nozzle 304 can be controlled such that a continuous fiber can be in contact with the substrate 306 when a print direction of the continuous fiber is changed.

Figure 1D:
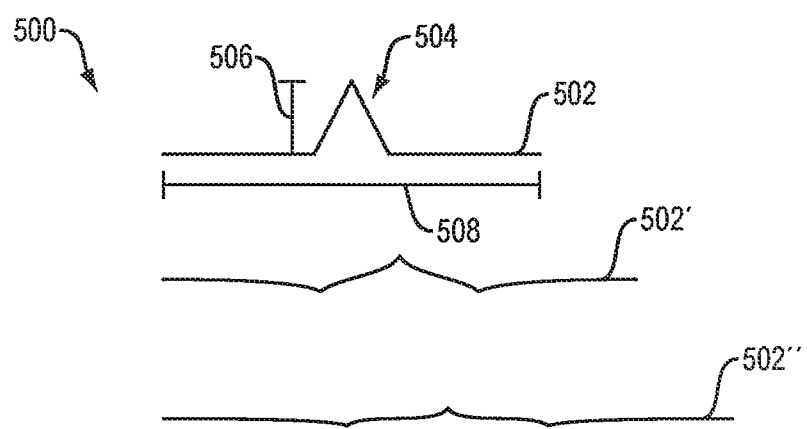
FIG. 1D is a schematic illustration of a finite element simulation of an embodiment of a fiber with a wave under application of a tensile force.
Figure 1E:
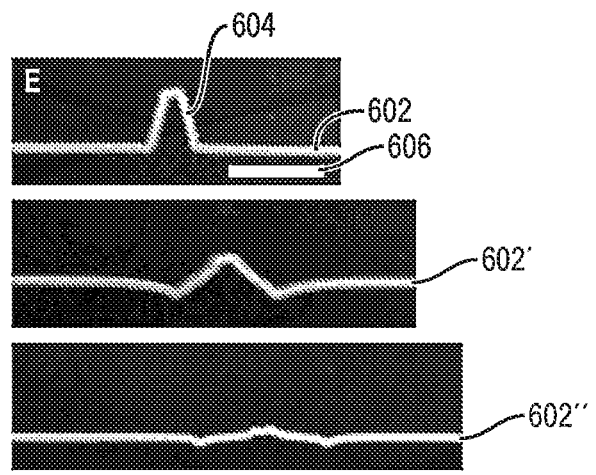
FIG. 1E are images of an embodiment of a fiber with a wave under application of a tensile force akin to the finite element simulation of FIG. 1D.

FIG. 1D shows a finite element simulation 500 of an exemplary embodiment of an individual fiber portion 502 with a wave 504 subject to a tensile force. The fiber portion 502 can have a length 508 that corresponds to a neutral or resting state of the fiber in which there is no external tensile force applied to the fiber. The wave 504 can have a height 506 in the neutral state. The finite element simulation 500 shows a mechanical response of the fiber 502 to application of a tensile force. As can be seen, from the fiber simulation at 502' and 502", the height of the wave 504 can decrease and the length of the fiber portion 508 can increase. The mechanical response 502' of the fiber can be dominated by a wave-bending mechanics, while the mechanical response 502" of the fiber can include greater influence of fiber-stretching mechanics. FIG. 1E shows images of an exemplary embodiment of an individual fiber portion 602 with a wave 604 subject to a tensile force. The images of the mechanical response 602', 602" generally correspond to the finite element simulation of FIG. 1D. In some embodiments, the wave feature 604 can extend across a length of less than about 5mm of the fiber portion 602. A scale bar 606 with a length of about 5 mm is shown in FIG. 1E for reference. In other embodiments, a wave feature can extend across a length equal to or greater than about 5mm of a fiber portion.

Figure 2A:
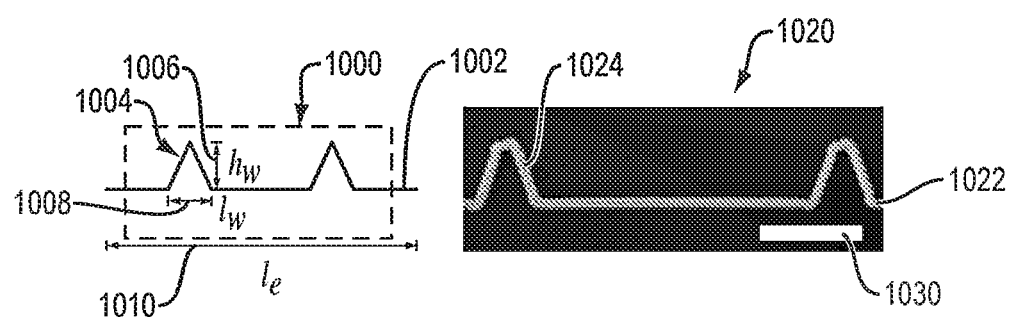
FIG. 2A is both a schematic illustration and an image of yet another embodiment of a fiber with a wave feature under application of a tensile force with a more detailed view of the wave feature.

As introduced above, fabrics or mesh manufactured in accordance with the present disclosure can include one or more fiber portions with one or more wave features. For example, FIG. 2A shows a schematic of an embodiment of a unit cell element 1000 having a fiber portion 1002 with a wave 1004. The wave 1004 can be repeated twice along the length of the fiber portion 1002. The wave 1004 can have a height or amplitude 1006 and a length 1008 when the fiber 1002 is in a neutral state without application of a tensile force. The fiber 1002 can have a full length 1010, which can extend beyond the boundaries of the illustrated schematic 1000. FIG. 2A also shows an image 1020 of a fiber 1022 with a wave 1024. The portion of the fiber 1022 illustrated in the image 1020 can include two waves 1024. A scale bar 1030 of approximately 5mm is shown for reference. In some embodiments, such as the image 1020, the wave 1024 can have a neutral length of less than or equal to about 5 mm. Further, in some embodiments, a distance between consecutive waves 1024 can be greater than the length of the wave 1024. In other embodiments, dimensions of a wave and/or spacing between adjacent waves can be different than that illustrated in FIG. 2A.

Figure 2B:
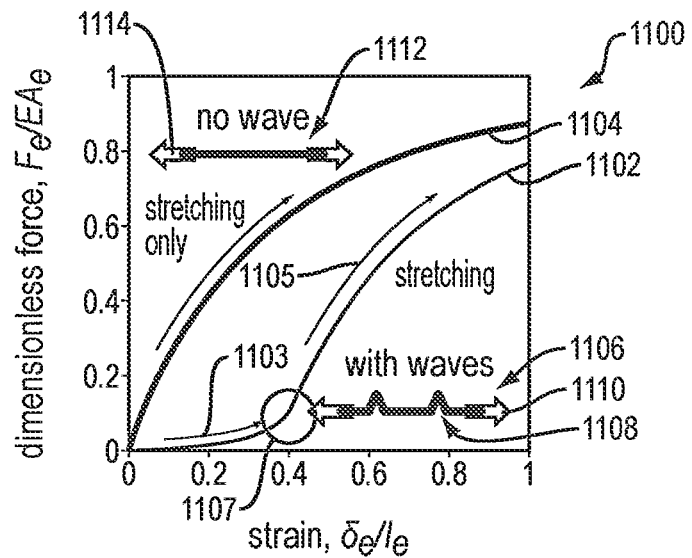
FIG. 2B is a plot with a model tensile response of a fiber with wave features in accordance with the present disclosure and a conventional fiber without wave features.

The addition of one or more curved features, such as wave 1004, to one or more fibers in a mesh can allow for control of a non-linear tensile response of the one or more fibers. More particularly, waves can be added to one or more fibers of a mesh such that the fiber can bend with a lower stiffness before it stretches. The amplitude or height of the waves (e.g., the height 1006 of the wave 1004) can control the strain at which the higher stiffness occurs in a fiber and, accordingly, a unit cell and fabric. FIG. 2B illustrates a model tensile response 1102 of a fiber 1106 with wave features 1108 and a model tensile response 1104 of a fiber without a wave feature. More particularly, a plot 1100 shows a fiber strain per unit length ($\delta_e/l_e$) against a force applied to the fiber. The model tensile response 1102 can be in response to a tensile force 1110 applied to the fiber 1106. As can be seen, the tensile response 1102 of the fiber 1106 can be non-linear. The tensile response 1102 can include a "wave-bending" phase 1103 in which the one or more wave features 1108 of the fiber 1106 can bend in response to a tensile force. Subsequently, the tensile response 1102 can include a "stretching phase" 1105 in which the fiber 1106 itself can stretch with an increased strain on the fiber as compared to the strain in the wave bending period 1103. A transition period 1107 can occur during which the tensile response changes from the wave-bending phase 1103 to the stretching phase 1105. In contrast, the model tensile response 1104 of a fiber 1112 without waves can have a response that consists only of stretching of the fiber 1112. As can be seen from FIG. 2B, at least for a response dominated by fiber stretching, the fiber with waves 1106 can experience a larger amount of strain for a given force than the fiber without waves 1112.

Figure 2C:
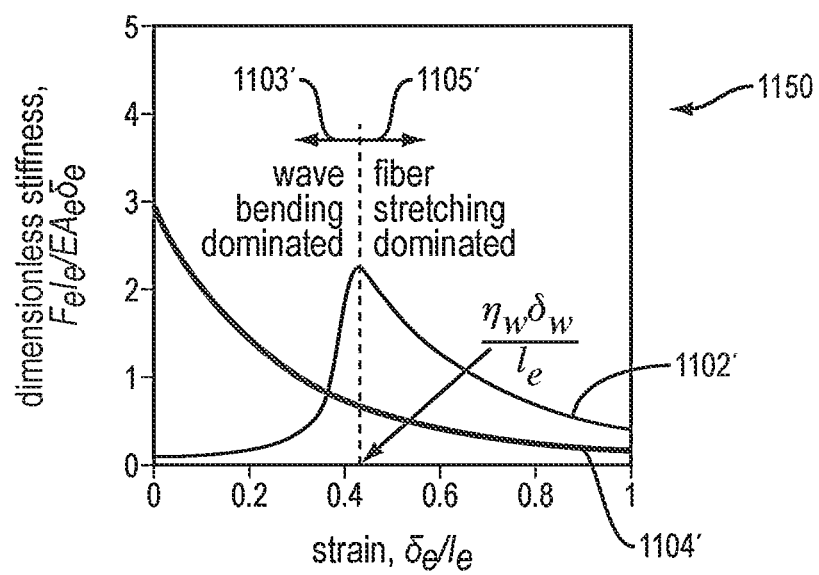
FIG. 2C is a plot with a model stiffness of the fibers of FIG. 2B.

FIG. 2C provides a plot 1150 that illustrates a stiffness of fibers with a configuration similar to the fibers 1106, 1112 of FIG. 2B. More particularly, the exemplary fiber 1106 with at least one wave feature 1108 can have a stiffness response 1102' as a function of an amount of strain on the fiber. A max stiffness can occur at a transition strain $\delta_t$ that can correspond to the transition from the wave-bending phase 1103 to the stretching phase 1105. As can be seen, the stiffness 1102' of the fiber 1106 with waves can increase from a point with negligible amount of strain, or approximately zero strain, on the fiber, up to the transition strain $\delta_t$ during the wave bending dominated response 1103', which can correspond to the wave-bending phase 1103, described above. The stiffness 1102' of the fiber can decrease from the maximum point during the fiber stretching dominated phase 1105', which can correspond to the stretching phase 1105, described above. The fiber-stretching dominated phase 1105' can occur as the fiber experiences strain beyond the transition strain $\delta_t$. The transition strain $\delta_t$ can be approximated using the equation $(n_w * \delta_w)/l_e$, where represents the number of wave features along a fiber portion extending through a unit cell, $\delta_w$ represents the length of one of the wave feature(s) 1108, and $l_e$ represents a length of the entire fiber. In contrast to the stiffness 1102' of the fiber 1106 with waves, the fiber without waves 1112 can exhibit a stiffness 1104' in response to strain. The stiffness 1104' of the fiber without waves 1112 can initially be very high, in comparison to that of the stiffness 1102', and can subsequently decrease with application of strain. More particularly, the fiber without waves 1112 can have a maximum stiffness at a point where there is little strain on the fiber, and can decrease in stiffness at a higher rate as strain is first applied.

As discussed above, a tensile response of a fiber including one or more wave feature 1004 can include a transition phase 1107 in which the tensile response transitions from the wave bending phase 1103 to a subsequent fiber-stretching phase 1105. An amount of strain at which this transition phase occurs can be controlled, at least in part, by varying the height or amplitude 1006 of the wave 1008. Control of the transition phase in this manner can be described with reference to FIGS. 2D-2F.

Figure 2D:
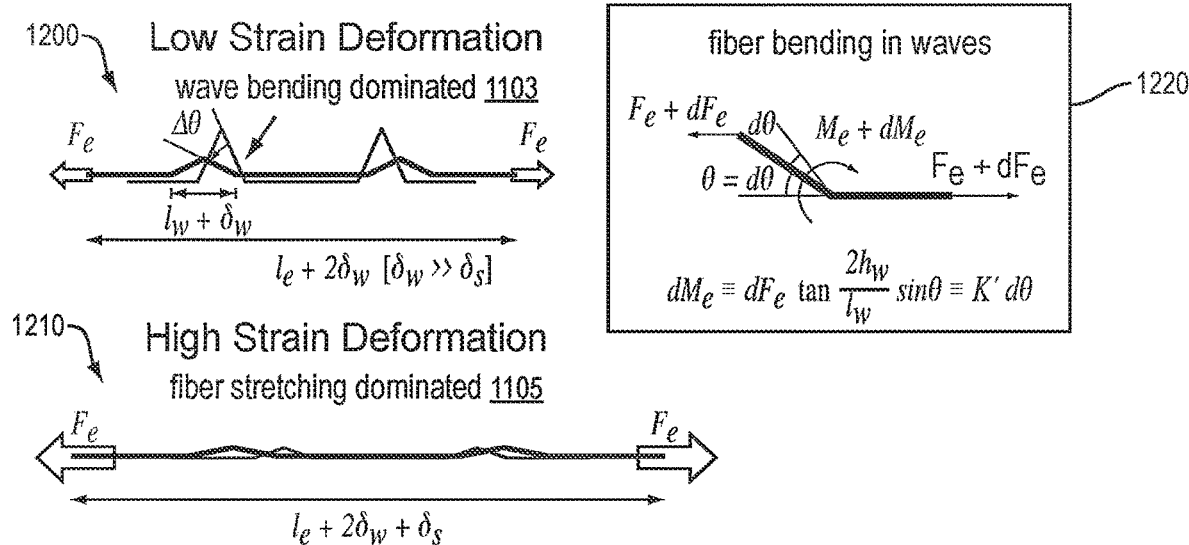
FIG. 2D is a schematic illustration of a fiber with a wave undergoing low-strain deformation and high-strain deformation.

FIG. 2D provides a schematic model 1200 illustrating deformation of a fiber with waves during the wave-bending phase 1103, which can occur as low strain deformation. FIG. 2D also shows a schematic model 1210 illustrating deformation of the fiber with waves during the fiber-stretching phase 1105, which can occur as high strain deformation. The fiber mechanics of the wave-bending phase 1103 is further detailed in a schematic model 1220. As illustrated by FIG. 2D, the deformation of a fiber with waves can be dominated by the wave-bending response at low strains, while, at high strains, the deformation can be dominated by the fiber-stretching response or behavior.

Figure 2E:
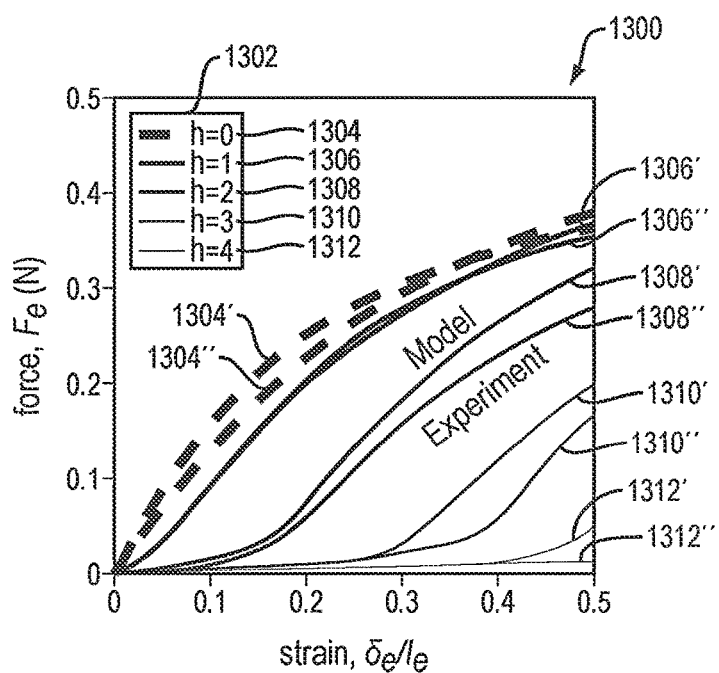
FIG. 2E is a plot showing a strain response to a tensile force of fibers with varying wave heights for modeled and experimental fibers.

FIG. 2E is a plot 1300 showing exemplary strain responses of a fiber with one or more wave features to a tensile force. The plot 1300 shows a strain response for five different fibers with waves of varying height. The height of the wave 1006 can be represented by a variable "h," such that the height 1006 of the wave 1004 can increase as the h number increases. The key 1302 labels the five fibers, from smallest wave height to largest wave height, as 1304, 1306, 1308, 1310, and 1312. A model or predicted strain response—1304', 1306', 1308', 1310', 1312'—and an experimental strain response—1304", 1306", 1308", 1310", 1312"—are shown on the plot 1300 for each of the five fibers. As can be seen from the plot 1300, a transition from a low-strain response to a high-strain response can occur at increasing strain with an increase in the height 1006 of the fiber wave 1004.

Figure 2F:
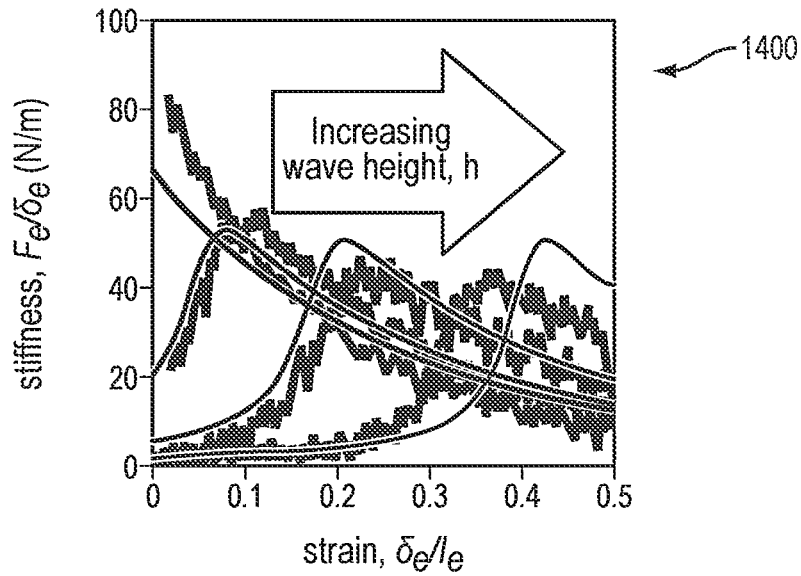
FIG. 2F is a plot showing stiffness of the fibers plotted in FIG. 2E.

FIG. 2F provides a plot 1400 that illustrates a stiffness of the five fibers of FIG. 2E relative to strain. Similarly, a maximum stiffness of a fiber can occur at higher strain as the height 1006 of the wave feature 1004 increases. In other words, the higher the wave height h, the higher the strain at which the maximum stiffness of the fiber occurs.

In some embodiments, stiffness of a unit cell can be increased by providing additional fiber portions to a unit cell element. More particularly, one or more adjacent filaments or fiber portions in a unit cell can be bonded, which can provide for control over a ratio of the bending stiffness and stretching stiffness. In this manner, the number of bonded adjacent filaments in an element of a unit cell can be controlled to further tune the non-linear tensile response of the element, as shown and described above with respect to FIG. 2A. Varying the number of filaments and their connectivity can also provide significant control over element bending stiffness independently of tensile stiffness. For example, an element composed of several smaller filaments can be more flexible in bending than an element composed of a single larger diameter monofilament. This decrease in bending stiffness can decrease the tensile stiffness of the unit cell at low strains, largely independently of the tensile response of the unit cell at higher strains, which can depend primarily on a cross-sectional area of the fiber(s) as well as their material composition. In some embodiments, changing stiffness of the unit cell at higher strains can be accomplished by changing the material composition of the fiber or the fiber cross-sectional area. For example, a stainless steel fiber with a much higher tensile modulus than an elastomer can be integrated into a mesh to increase the high strain stiffness of the mesh. The higher tensile modulus of the stainless steel can increase stiffness of the mesh when a tensile force is applied.

Figure 2G:
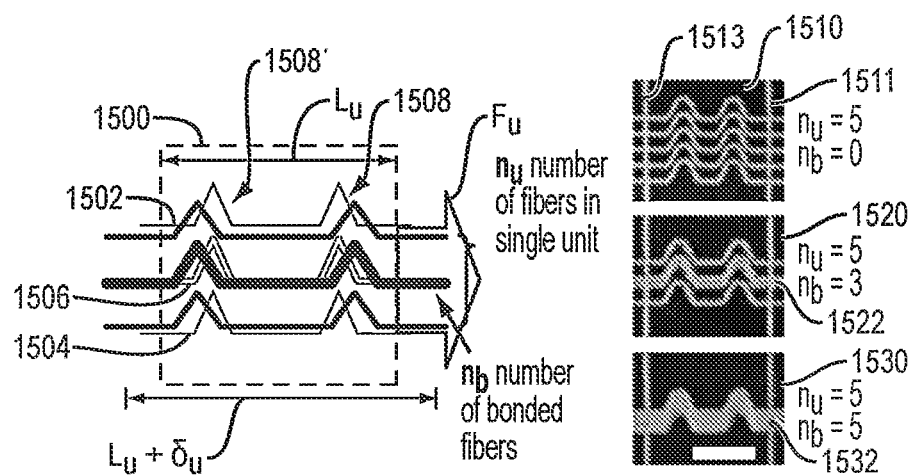
FIG. 2G is a combination of schematic illustrations and images of fibers showing variations in fiber bonding.
Figure 2H:
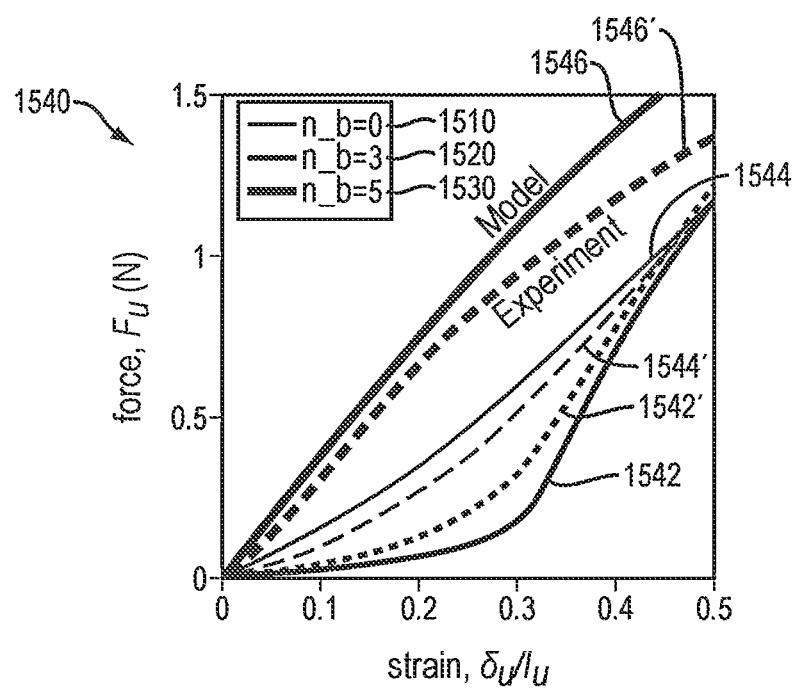
FIG. 2H is a plot showing a strain response of elements with a varying number of bonded fibers for modeled and experimental fibers.

FIGS. 2G and 2H illustrate how variations in fiber bonding within a unit cell of a mesh can be used to control tensile response properties of the fibers.

Turning first to FIG. 2G, an exemplary unit cell 1500 can include a number of fibers nu extending through the unit cell. Each fiber can have a resting length $l_u$, which can define a length of the unit cell fiber portion. A tensile force $F_u$ can be applied to the fibers extending through the unit cell 1500 such that the length of the unit cell fiber portion can be extended from the resting length $l_u$ to a tensile length $l_u + \delta_u$, where $\delta_u$ represents a strain or length extension of the fiber that can result from the tensile force. The fiber portions $n_u$ extending through the unit cell 1500 can include one or more single fiber portion, such as, for example, fiber portions 1502 and 1504, as well as one or more bonded portion, for example bonded portion 1506, that can include a plurality of bonded single fiber portions $n_b$. One or more of the fiber portions extending through the unit cell 1500 can include a wave feature, for example the wave feature 1508. As shown in FIG. 2G, each of the fibers nu can include the wave feature 1508, which in the illustrated embodiment is repeated twice along the length $l_u$ of each fiber portion to include a second wave feature 1508'. While two wave features 1508, 1508' are illustrated in each of the fibers nu of the unit cell 1500 in FIG. 2G, a lesser or greater number of wave features can be included in one or more fiber portion extending through a unit cell. Three exemplary unit cell images-1510, 1520, and 1530—are shown in FIG. 2G, with each unit cell having five fiber portions extending therethrough but with varying fiber configurations. In other words, for each unit cell, 1510, 1520, 1530, the number of fiber portions extending through the respective unit cell ($n_u$) is equal to five, but the number of bonded fiber portions ($n_b$) can vary.

More particularly, the first unit cell 1510 can have no bonded fiber portions ($n_b$=0), such that each of the five fibers extending through the unit cell can each be a single fiber portion. The second unit cell 1520 can have three bonded fiber portions ($n_b$=3), which together can form a bonded portion 1522. A single fiber 1524, 1526 can extend above and below the bonded portion 1522, respectively. Finally, the third unit cell 1530 can have five bonded fiber portions ($n_b$=5), which together can form the bonded portion 1532. As can be seen, each of the fiber portions $n_u$ extending through the unit cells 1510, 1520, 1530 can include two wave features along the length of the fiber portion within the unit cell $l_u$. Each unit cell can also have two additional fibers, for example fibers 1511 and 1513 in the first unit cell 1510, that can extend vertically through the unit cell. In other words, the additional fibers 1511, 1513 can extend at an angle, and, in some embodiments, orthogonally, relative to the fibers $n_u$ extending through the unit cell. In some embodiments, the additional fibers 1511, 1513 can extend straight through the unit cell such that there is no wave feature along the additional fiber. As will be discussed with reference to FIGS. 2H, variation in the number of bonded fiber portions $n_b$ within a unit cell can be used, for example, to control the unit cell response to a force applied to the unit cell.

FIG. 2H is a plot 1540 showing the relationship between a force applied to a unit cell and unit cell strain for the unit cells 1510, 1520, and 1530 of FIG. 2G, representing zero bonded fiber portions, three bonded fiber portions, and five bonded fiber portions, respectively. For each of the unit cells, a model or predicted strain and an experimental strain are shown. The unit cell 1510 can have a model strain 1542 and an experimental strain 1542; unit cell 1520 can have model strain 1544 and an experimental strain 1544; and unit cell 1530 can have a model strain 1546 and an experimental strain 1546'. As can be seen from the plot 1540, as the number of bonded fibers in a unit cell decreases, the bending stiffness of the unit cell can decrease, and, accordingly, the tensile stiffness of the fibers as a whole can decrease at low strains. Similarly, the greater the number of bonded fibers in a unit cell, the higher the bending stiffness of the unit cell and thus, the higher the tensile stiffness at low strains. Accordingly, adjusting the number of bonded fibers in a unit cell can control the unit cell stiffness at low strains.

In some embodiments, control over adjacent fiber bonding can be achieved through control of a toolpath of a tool used to lay down or extrude fibers, such as, for example, the extruder 300. For example, to ensure that adjacent fibers are not bonded, the toolpath can create distance between the fibers as they are deposited such that the fibers only come into contact with one another after the fiber has cooled and, accordingly, can no longer adhere to an adjacent fiber. This can be achieved, for example, by temporarily increasing a z-height of the nozzle 304 (i.e., increasing the distance between the distal end of the nozzle 304 and the proximal-facing surface of the substrate 306) as the fiber 302 is extruded, and only bringing the nozzle 304 back down towards the substrate 306 once the extruded fiber 302' has cooled. By way of further example, the extruder 300 or other tool can lay fibers with a gap extending between adjacent fibers. In contrast, for bonding of adjacent fibers, the tool can lay adjacent fibers such that no gap exists between the adjacent fibers and/or in a manner such that a fiber comes into contact with an adjacent fiber when the fiber has not yet cooled. In some embodiments, the mesh can include bonded adjacent fiber portions that are non-stochastically and rationally distributed with respect to a volume of the mesh material. As discussed above, fibers that are not bonded to one another can be more flexible in bending than otherwise identical fibers that are bonded to one another. Thus, by reducing bonding of adjacent fibers, meshes can become more flexible. In some embodiments, a mesh can be flexible such that the mesh can drape over structures making the mesh conformable and comfortable to wear.

Additionally, or alternatively, the element mechanical response of the unit cell can be controlled by varying a material composition of one or more fiber portions of the element. For example, one or more pre-made fibers can be patterned into a fabric using a passive deposition process. Pre-made fibers can have higher strengths than additively manufactured materials, for example, due to the molecular alignment induced when a pre-made fiber is drawn. Such molecular alignment can allow for efficient load transfer between molecules via covalent bonds, which can be very strong. In some embodiments, pre-made fibers can be metallic, which can have a high strength and modulus. In prior additive manufacturing processes, the molecular alignment achieved in a pre-made fiber is not possible due to, for example, heat required to generate bonding in the AM process and/or a lack of an alignment mechanism, such as those present in sintering or UV-based processes. Incorporating continuous fiber into meshes or fabrics as provided for herein can allow for higher tensile stiffness at lower bending stiffness than previously possible. Patterning pre-made fibers can present challenges, however, as pre-made fibers are not typically adhesive, and conventional thermoplastic processing to make them adhesive can degrade the molecular alignment and, therefore, desirable mechanical properties. Accordingly, existing methods to incorporate continuous fiber into AM parts have relied on sheathing the pre-made fiber in a thermoplastic matrix for adhesion, resulting in large increases in flexural stiffness that make this method unsuitable for fabrics.

The present disclosure provides for a printing process that can allow for the deposition of continuous fiber, including pre-made fiber, by using an adhesive substrate that can passively pull fiber out of a nozzle. As such, unwanted increase in flexural stiffness can be avoided as use of a thermoplastic sheath can be omitted when laying down or extruding pre-made fiber. In some embodiments, the substrate can be made adhesive by depositing an adhesive from a nozzle prior to deposition of the continuous fiber. In printing processes of the present disclosure, moving the nozzle 304 over the substrate 306 can cause the fiber 302 to follow the path of the nozzle, which can enable patterning of the fiber in a desired manner. Patterning of the fiber can include, for example, creating one or more fiber portion with one or more wave feature 1004 in each unit cell of the mesh. Continuous fiber can be sandwiched between two layers of another material, such as a thermoplastic, to bond the fiber to the rest of the fabric. The bonded fabric can be deposited before and after deposition of the continuous fiber. In other embodiments, the thermoplastic or other material can be positioned separate from depositing the continuous fiber. The height of the nozzle 304 relative to the substrate 306 (also referred to as a printhead z-height) can be significant with respect to mechanical response properties of the fiber 302' being deposited onto the substrate 306. For example, bringing the nozzle 304 too close to the substrate 306 can raise a temperature of the fiber 302' to an extent that the fiber can lose strength. On the other hand, if the nozzle 304 lays the fiber 302' at a distance too far from the substrate 306, the fiber 302' may not bond with the new layer. In some, non-limiting embodiments, a z-height difference of approximately 0.3 mm can be employed. Additional details about the printing process that can be used to print the materials, braces, etc. provided for herein can be found in U.S. Patent Application Publication No. 2017/0165908, the content of which was incorporated by reference above. Some, but not all, of that information is at least described below in discussing various non-brace applications with which meshes of the present disclosure can be used.

Applications of Mesh with a Non-Linear Tensile Response

The meshes and fabrics provided for herein, which can have a non-linear tensile response, can be used to make or can be incorporated into ankle braces that leave the ankle unrestrained until a certain degree of rotation, at which point the stiffness of the brace can increase to prevent further rotation and injury. In this manner, such braces can be used to help prevent ankle inversions.

Figure 3A:
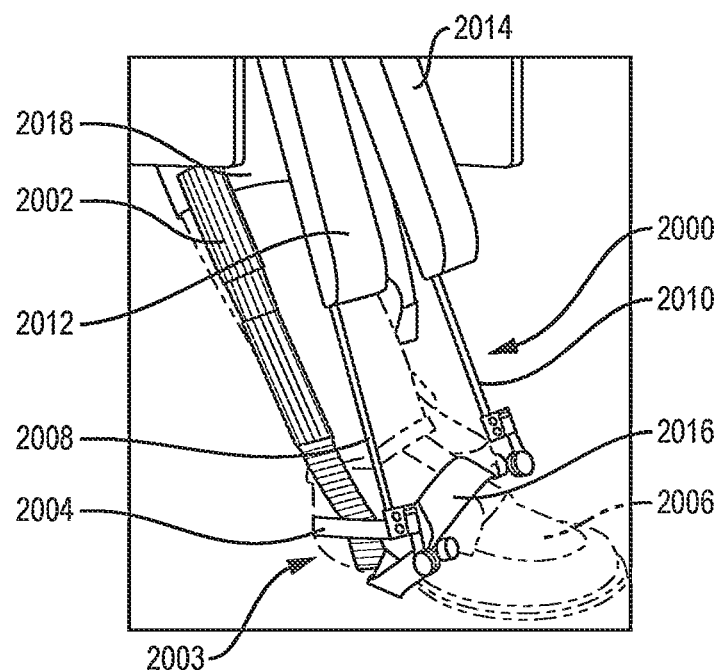
FIG. 3A is a perspective view of one exemplary embodiment of a brace including a non-linear mesh, the brace being attached to a leg and foot.

FIG. 3A shows a testing set-up 2000 for testing an embodiment of an ankle brace including mesh 2002 of the present disclosure. The ankle brace can include one or more portion of fabric or mesh 2002 that can be manufactured in accordance with the present disclosure to have a non-linear tensile response and other desired properties, such as a desired stiffness, strain, etc. For example, in the embodiment of FIG. 3A, the mesh 2002 can form the ankle brace and can extend from a user's ankle 2003 longitudinally along a leg of the user. The mesh 2002 can be attached at one or more locations to the user. For example, a first anchor 2004 can adhere or otherwise securely attach the mesh 2002 to the user's foot or shoe 2006. A second anchor (not visible) can attach the mesh 2002 to a location along the leg of the user. Anchors can include any structure or component(s) capable of holding the mesh 2002 at a desired location with respect to the user's anatomy, including but not limited to tape, hook and loop fasteners, screws and washers, etc. While the ankle brace of FIG. 3A includes mesh 2002 that can be directly attached to the user, in other embodiments a brace can include mesh of the present disclosure, such as mesh 2002, securely attached to or printed on/with a conventional fabric (such as an existing brace or wearable).

The testing set-up 2000 can include a robotic ankle exoskeleton testing device having metal rods 2008, 2010 extending from components 2012, 2014, respectively, and can couple the testing device to the user's foot 2006 and ankle 2003. The testing device can also include a strap 2016 that can secure the device across the shoe 2006. The robotic ankle exoskeleton can be used to measure the stiffness of the ankle 2003 by imposing a torque on the ankle and measuring resultant angular displacement of the ankle. A conventional knee brace (i.e., a brace without mesh or fabric of the present disclosure) 2018 can be used to support the testing device.

While the brace as shown in FIG. 3A has only a single piece of fabric or mesh 2002, it will be appreciated that braces as provided for herein can include one or more additional pieces of fabric, for example, on an opposing side of the leg not visible in FIG. 3A. In contrast to existing ankle braces that immobilize the entire ankle joint, the mesh 2002 can limit ankle inversion only as-needed to prevent injury, while leaving the ankle motion otherwise unimpeded. This can be achieved by manufacturing and placing the fabric 2002 of the brace such that particular portions of the fabric having particular properties align with desired portions of the patient anatomy. Moreover, the mesh of braces in accordance with the present disclosure, such as the mesh 2002, can allow for the ability to customize shape and mechanics of the brace to individual patients, taking into account factors including but not limited to a patient's particular ankle and leg geometry, stiffness, injury, etc. Such customization can be achieved by controlling the design and manufacture of mesh at the element, unit cell level, and/or regional level. Additionally, or alternatively, customization can be achieved by controlling design, manufacture, and/or placement of one or more pieces of mesh of the present disclosure onto a wearable or implantable device. Accordingly, braces can be designed with improved mechanics while being more economical than existing customized braces that are assembled by hand.

Figure 3B:
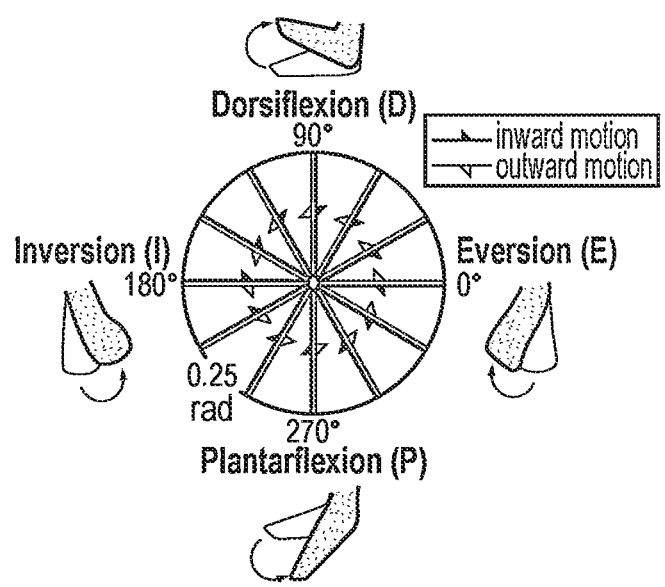
FIG. 3B is a schematic diagram of a two-dimensional space of ankle inversion-eversion and dorsiflexion-planar range of motion of an ankle, which can be used, for example when a stiffness of an ankle is being tested using the brace of FIG. 3A.
Figure 3C:
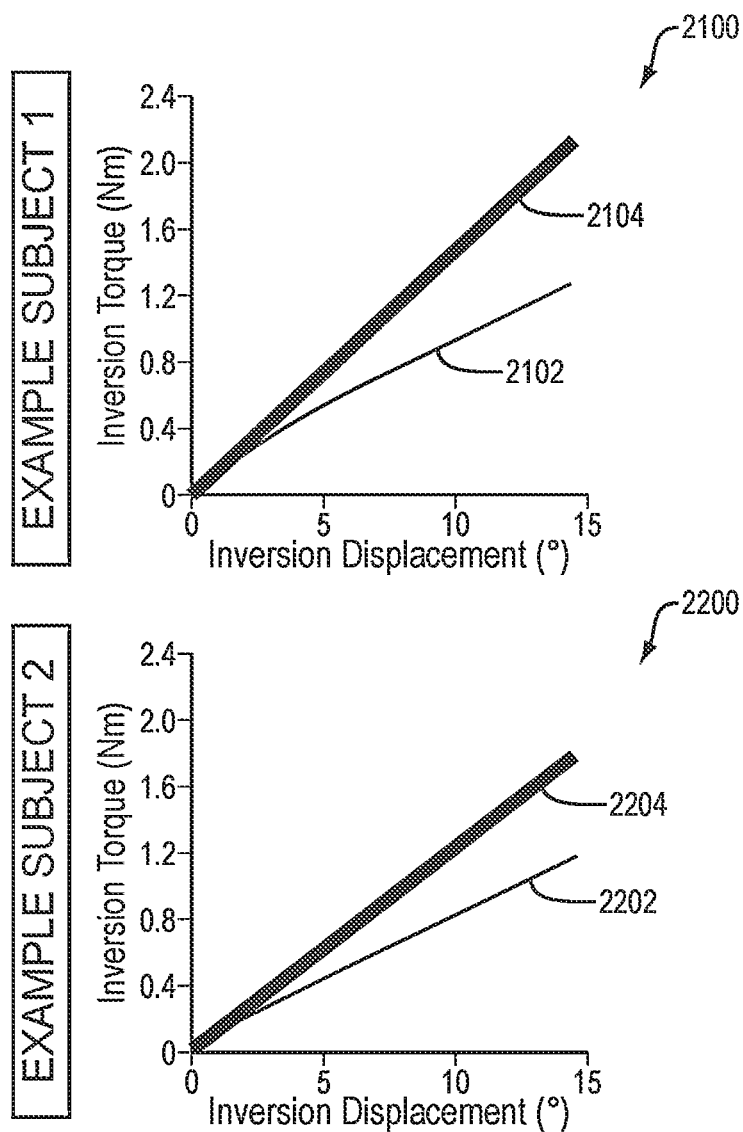
FIG. 3C shows plots of applied ankle torque and a resulting angular displacement in the inversion direction for two human subjects, one wearing a brace in accordance with the present disclosure and one not wearing a brace.
Figure 3D:
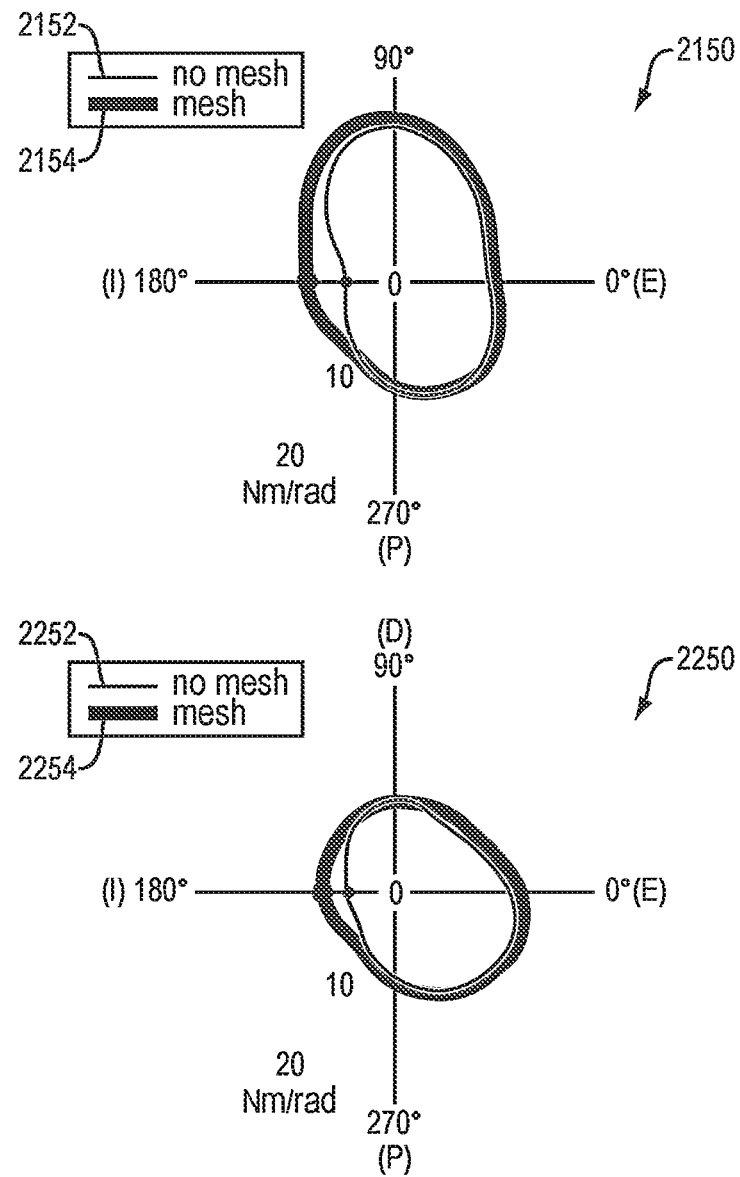
FIG. 3D shows a stiffness distribution of the ankle of the tests in FIG. 3C.

FIGS. 3C and 3D illustrate mechanical response features of the ankle brace 2002 of FIG. 3A in the space of ankle motion defined by FIG. 3B.

FIG. 3B schematically shows a subset of 12 directions in which an ankle can be rotated to generate stiffness measurements of the ankle in the two-dimensional inversion/eversion-dorsiflexion/plantarflexion (IE-DP) space of ankle rotation. Accordingly, ankle stiffness when wearing a brace of the present disclosure can be compared to ankle stiffness of an ankle without a brace. Fibers with non-linear mechanics, as described herein in accordance with the present disclosure, can be distributed around the ankle, with the fibers having different wave heights, fiber thickness, material composition, fiber bonding, and/or fiber orientations to prevent excessive motion in one or more direction as required by the needs of a particular patient. While discussion with respect to FIGS. 3A-3D is directed to an ankle, fibers with non-linear mechanics can be placed on other parts of the body, such as the neck, back, knee, etc., to similarly allow free motion in a certain direction up to a certain point, beyond which fiber stiffness can increase to prevent further motion in the direction. Accordingly fibers as disclosed herein can be incorporate into various wearable or implantable devices (e.g., a brace, adhesive tape, implant, etc.) to prevent injury from motion beyond a desired range in one or more directions.

FIG. 3C shows a plot 2100 illustrating a relationship between ankle inversion torque as it relates to an angular inversion displacement of the ankle. Plot 2100 corresponds to testing performed on a first human subject wearing the ankle brace with mesh 2002 with the testing set-up 2000, as shown in FIG. 3A. While the results illustrated are a direct impact of the ankle brace, a person skilled in the art will understand that various test subjects using the same brace may have different results depending, at least in part, on the age, injury, and other personal characteristics of the test subject. The results illustrated in FIG. 3C nevertheless demonstrate the advantages of braces including mesh like the mesh 2002 illustrated in FIG. 3A. A line 2102 reflects torque and displacement of the ankle without any brace, while the line 2104 reflects the relationship between torque and displacement of the ankle wearing the brace including the mesh 2002. For small values of inversion displacement, lines 2104 and 2102 are similar, but for higher values of inversion displacement, the ankle with the mesh 2002 response, line 2104, can diverge from the ankle without a brace response 2102. This can validate that the brace with mesh 2002 of the present disclosure added non-linear stiffness to the ankle joint in the inversion direction as intended. Plot 2200 corresponds to testing performed on a second human subject. A line 2202 reflects torque and displacement of an ankle without a brace, while a line 2204 reflects the relationship between torque and displacement of the second subject's ankle while wearing the brace with mesh 2002 of the present disclosure. Results similar to those discussed above with respect to plot 2100 can be seen.

The brace can be designed with mesh 2002 of the present disclosure having non-linear characteristics such that at low inversion displacement the brace does not significantly affect ankle mechanics. At high inversion displacement, however, the mesh 2002 can increase the torque required to rotate (i.e., angularly displace) the ankle. This can be seen in plots 2100 and 2200, which show that the torque required to achieve ankle inversion can be similar for an ankle without a brace (2102, 2202) and an ankle with a brace of the present disclosure (2104, 2204) up to an angular displacement of about 3 degrees. Beyond this point, the torque needed to further invert the ankle is higher for an ankle wearing the brace with mesh 2002 than an ankle without a brace. In the brace with mesh 2002 worn by the example subjects of FIG. 3C, the mesh increase in stiffness can occur at about 3 degrees inversion displacement. The inversion displacement at which a brace or mesh of the present disclosure increases in stiffness, however, can be controlled through one or more of the factors outlined above, for example, wave weight, fiber bonding, fiber composition, etc.

FIG. 3D shows two plots 2150,2250 of the directional variation in ankle stiffness in the IE-DP space, with the plots 2150, 2250 corresponding to the testing of subject one and subject two of FIG. 3C, respectively. More particularly, the stiffness plot 2150 shows a stiffness 2152 of the ankle of subject one without a brace and a stiffness 2154 of the ankle of subject one wearing the brace with mesh 2002 of the present disclosure. The stiffness plot 2250 shows a stiffness 2252 of the ankle of subject two without a brace and a stiffness 2254 of the ankle of subject two wearing a brace of the present disclosure with mesh. The plots 2150, 2250 illustrate that the mesh 2002 can selectively increase the stiffness of the ankle in a single direction, in this instance an inversion direction, while leaving motion of the ankle relatively unchanged in other directions. Selectively reinforcing the ankle in this manner by incorporating fibers with non-linear response characteristics can significantly improve the comfort of support devices. The plots 2150, 2250, and, more particularly, the ankle stiffness represented by each line 2152, 2154, 2252, 2254, can be derived from applied torque to angular displacement curves, such as those shown in FIG. 3C for the inversion direction, for an ankle in each of the 12 directions illustrated in FIG. 3B. The slope of each of the applied torque to angular displacement curve is a linear approximation of ankle stiffness, and can be plotted to create the stiffness distribution lines 2152, 2154, 2252, 2254 of FIG. 3D.

In some embodiments a conductive material can be placed onto, or otherwise associated with, the brace to serve as one or more strain sensors. This can help demonstrate the further versatility that can be achieved through material composition control. Alternatively, or additionally, one or more conductive stainless-steel threads can be incorporated into the brace or mesh, which can be used to heat joints for thermotherapy.

As discussed above, integration of adjacent unit cells into fabrics can form larger scale functional units that can have a known and controlled mechanical response in accordance with the properties of the unit cells. This can allow for various medical devices (e.g., wearables, implantables) to be produced, such as, by way of non-limiting example, an ankle or knee brace. In one non-limiting exemplary embodiment, an ankle brace can include mesh of the present disclosure that can be stiff to minimize transverse motion of the knee, but flexible along the vertical line (i.e., along a longitudinal axis of the leg, for example extending approximately through a length of a femur and tibia) such that the brace support will inconvenience the user as little as possible. The support device can also be highly porous and can therefore be breathable enough to be comfortably worn.

Figure 4:
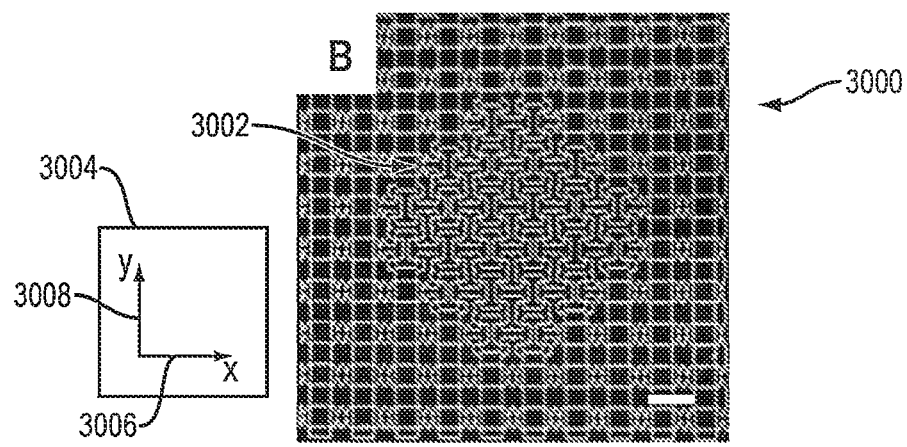
FIG. 4 is a top view of yet another exemplary embodiment of a schematic illustration of a mesh, this mesh including a locally patterned region having a negative Poisson's ratio.

FIG. 4 shows an embodiment of a mesh 3000 that can either form or be incorporated into a support device, such as a brace, adhesive tape, athletic tape (which is typically adhesive, but in some instances it may not be adhesive), or garment. The mesh 3000 can include a region 3002 that can be patterned with a negative Poisson's ratio. The region 3002 with the negative Poisson's ratio can allow the fabric to curve around patient anatomy, such as, for example, a knee, without folding and may thus increase comfort while reducing undesired motion.

Accordingly, applying a tensile force to the region 3002 in a first direction can cause the region to stretch in the first direction and to stretch or expand in a second direction that is perpendicular to the first direction. For example, and with reference to a coordinate system 3004 showing an X-axis 3006 perpendicular to a Y-axis 3008, a tensile force can be applied to the region 3002 in the X-direction 3006. The region 3002 can stretch in the X-direction 3006 in response to the tensile force and, as a result of the negative Poisson's ratio, can also expand or stretch in the Y-direction 3008. The mesh 3000 can also include unit cells having one or more fiber portions with wave feature(s), as discussed in detail above. With such a construction, the mesh 3000 can exhibit anisotropic mechanics.

Figure 5:
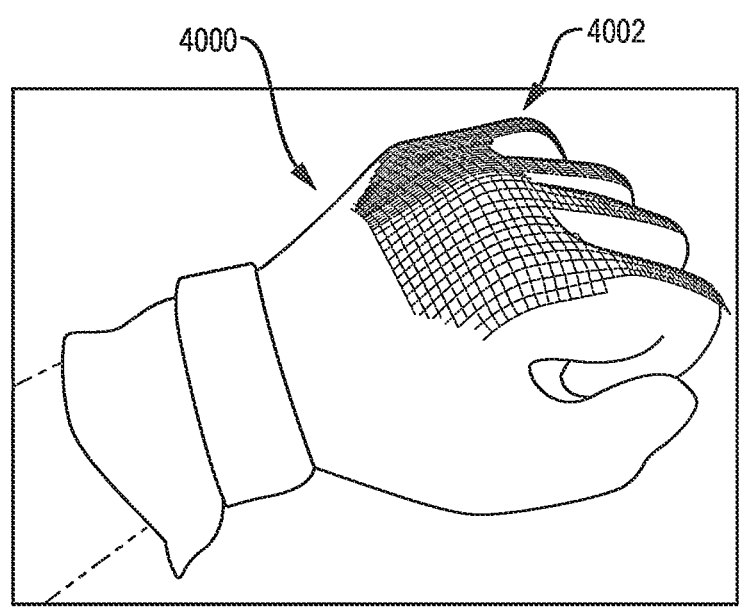
FIG. 5 is a perspective view of one exemplary embodiment of a glove having a mesh of the present disclosure incorporated therein.
Figure 6:
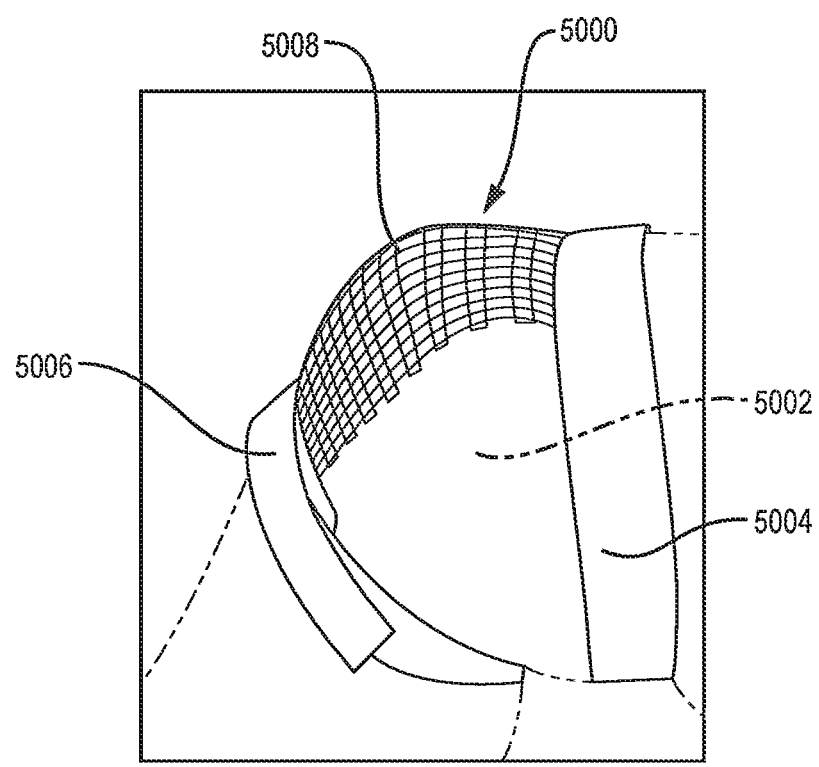
FIG. 6 is a perspective view of one exemplary embodiment of a mesh applied to a knee of a subject.

FIGS. 5 and 6 show non-limiting exemplary embodiments of wearable devices that can incorporate or otherwise be made of mesh of the present disclosure.

FIG. 5 shows a glove 4000 with a mesh 4002 that can be sewn onto or otherwise incorporated with the glove 4000. The mesh 4002 can be manufactured and placed such that the mesh can provide force to enable fingers of a user placed within the glove 4000 to unclench, and thus not be as encumbered as they would in braces that pre-date the present disclosure. As shown, the mesh extends over a portion of the back of the hand (e.g., where the carpals are located), over the knuckles, and towards the fingers (e.g., at least where the metacarpals are, and also the phalanges, although they are not visible). The locations where the mesh are placed allow for the selectively stiffening based on the manufacturing of the mesh, thereby allowing more freedom of movement for the wearer while also providing the necessary support at selection locations. The mesh 4002 can be manufactured and designed to include any of the properties, taken alone or in combination, of meshes and fabrics described herein. Further, a person skilled in the art will appreciate other designs in conjunction with a glove or other form of wrist brace made possible by the present disclosures.

In some embodiments, the mesh 4002 can be printed onto a knuckle template. A toolpath used to print the mesh 4002 can be three-dimensional by moving the printhead in three-dimensions (e.g., along an x-axis, a y-axis, and a z-axis of a traditional cartesian coordinate system) when printing the mesh as a single layer rather than printing the mesh 4002 as a series of planar layers. Printing the mesh 4002 in this manner can allow for the mesh to curve around the knuckles and provide for a better fit, while minimizing discontinuities in the mesh that could affect the mesh mechanics. The mesh 4002 can be placed onto the glove 4000 such that the mesh can be intended to provide extension forces to help a wearer to unclench their fist. This can be beneficial to users who have difficulty with this motion, which can be a consequence of neurological injuries such as acute ischemic stroke.

FIG. 6 shows a mesh 5000 manufactured in accordance with the present disclosure placed on a knee 5002 of a user. As shown, the mesh is held in a location by Velcro® strips 5004, 5006 associated with opposed ends of the mesh and placed above and below the patella or kneecap. The mesh 5000 can conform to the knee 5002. In some embodiments, the mesh 5000 can include a region having a negative Poisson's ratio, such as region 3002 of the mesh 3000, that can allow the mesh 5000 to conform to the knee 5002 without folding. This can increase comfort for the user when wearing the mesh 5000. For example, as shown in FIG. 6, a region 5008 in the center of the mesh 5000 can have a negative Poisson's ratio, which can help the mesh conformally cover the kneecap as the kneecap flexes. In some embodiments, the region 5008 can be a diamond. A person skilled in the art will appreciate other designs that can be used in the context of a knee, including meshes that cover different areas of the knee, have different shapes and sizes, etc. Likewise such meshes can be associated with the knee using many different techniques, including a device that looks more like a standard kneed brace but with the mesh replacing the portion that extends over the patella (or another location where the desired response afforded by the mesh can be achieved). The use of the illustrated Velcro® strips is just one way by which the mesh 5000 can be held at a desired location with respect to the knee 5002.

Figure 7:
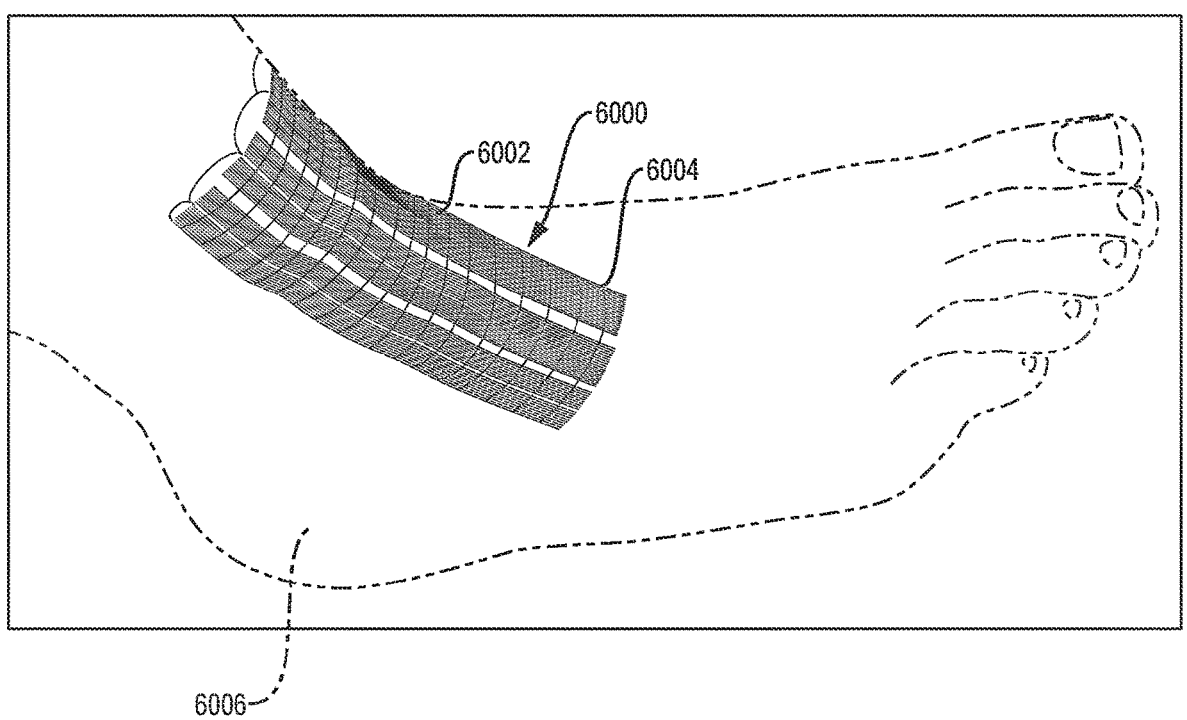
FIG. 7 shows another exemplary embodiment of a mesh of the present disclosure, the mesh being used as an athletic tape.

Similar principles can be applied to make braces for other parts of the body such as a wrist, knee, back, neck, etc., as well as adhesive tapes, athletic tapes (which may or may not be adhesive), stents, devices for use organs and muscles (e.g., breasts, abdomens), or other wearable or implantable devices. By way of further non-limiting example, FIG. 7 shows an athletic tape 6000 including a mesh 6002 of the present disclosure. As can be seen, the mesh 6002 can include one or more fiber portions 6004 with one or more wave features. The athletic tape 6000 is shown attached to a user and extending across the user's ankle 6006. Accordingly, a surface of the athletic tape 6000 that contacts the user can be adhesive. In some embodiments, the mesh 6002 can be attached to an adhesive substrate following the printing of the mesh, while in other embodiments the mesh 6002 can be printed directly onto an adhesive substrate. Any brace, tape, wearable or implantable device, etc. that incorporates one or more meshes of the present disclosure allows for reasonably, precisely controlled uniaxial tensile response at desired locations where the mesh is placed with respect to a subject's anatomy. The desired responses at the location of these meshes can include, for example, low stiffness at the location resulting from local and anisotropic non-linear mechanical responses via the mesh as provided for herein.

The use of the present disclosures in conjunction with an adhesive tape and/or athletic tape is one non-limiting example of a non-brace application. In such tape applications, a mesh of the present disclosure can be manufactured with an adhesive back to create an adhesive tape that can be placed to provide support to a treatment area without unduly restricting motion of surrounding anatomy. A person skilled in the art, in view of the present disclosures, will understand how adhesive tape is typically used. As provided for herein, the mesh itself could be incorporated into an adhesive tape, or it could be manufactured to be the tape itself. By way of non-limiting example, a mesh of the present disclosure can be printed onto or otherwise attached to conventional adhesive tape, such as athletic tape. Similarly, with respect to braces or other wearable devices, in some instances, an entire brace can be made with an AM process. Alternatively, structures of the nature provided for herein (i.e., meshes or fabrics) can be 3D printed onto a conventional textile or brace to control and/or enhance mechanics. For example, a mesh material as provided for herein can be additively manufactured onto an existing ankle brace, thereby enhancing the performance of a pre-existing device.

Another non-brace application provided for by the present disclosures is a surgical mesh, such as a hernia mesh. In view of the present disclosures, many different characteristics or properties of the mesh can be customized to provide user-specific or surgery-specific fits. The present disclosure allows for meshes that have local variation at various nodes where the fibers engage each other across a surface area of the mesh. Local variation can include, for example, bonding at certain nodes and not bonding at other nodes. Other characteristics of the mesh that can be varied include, for example, pore size to allow for customized fit of the mesh, the pores being the spaced between crossed filaments. Smaller pores can provide for greater stiffness than the remainder of the mesh, which can be useful, for example, in preventing a hernia from deforming the mesh and thus recurring. Larger pores, for example, can be used in portions that require closer integration with tissues. Mesh having larger pores can lead to less foreign body reaction, and having a mesh with the same stiffness as healthy tissue can lead to healthier tissue ingrowth. Then non-bonded nodes allow for flexibility of the mesh, which can be used, for example, to help minimize discomfort when worn post-surgery.

Prior to the present disclosure, small gaps were typically found at the nodes of crossing filaments. These gaps are referred to by those skilled in the art as interstices. The printing techniques provided for herein allows the resulting fabric to be devoid of interstices between the filaments that are bonded together. This is because, prior to the present disclosure, medical meshes were made as knitted or woven fabrics in which interstices were naturally formed at places where filament came into contact or close proximity. These interstices can harbor bacteria, which can be small enough to enter the interstices while keeping white blood cells out because the white cells can be too large to enter the interstices. This can lead to severe infections and mesh removal surgery. The methods of depositing adhesive material in the regions where filament meets provided for in the present disclosure allows the interstices to be eliminated by being filled with the adhesive or another material. The ability to create a fabric in a non-woven matter that is devoid of interstices at locations where filaments are bonded together is a useful development made possible by the present disclosure.

The displacement at which the stiffening occurs can be specified by modulating the bonding at interfilament nodes. This enables control of stiffness, pore size, and load capacity by introducing local slack into the filaments in a given area of the mesh, and controlling the diameter, density, and orientation of filament. By way of non-limiting example, the present disclosures allow for filament or fiber density of a resulting fabric to be less than or equal to an amount that produces a pore size of about 4 millimeters. Printing onto a 3D template can also be enabled so that the fabric conformably matches a desired surface (e.g., a 3D printed model of a patient's organ). Additionally, the surface area of the implant can be reduced by replacing knots and loops with straight monofilament. The use of loops in knitted mesh results in very high local surface area that leads to excessive foreign body reaction and tissue weakening. These loops also present microvoids large enough for bacteria to penetrate, but too small for white blood cells to reach, preventing the elimination of the bacteria from the body. In some embodiments, the mesh can contain no loops due to knitting, which can result in fewer microvoids or interstices.

The absence of loops can allow the mesh to have a larger pore size, which helps with tissue integration. The absence of loops also allows for the use of larger diameter filament in the mesh while achieving the same flexibility because each filament does not need to be as highly deformed to produce a desired mesh deformation. This can further reduce the needed surface area of an implant.

The local control of mechanics in 3D printed surgical meshes as provided for herein can help to mirror body mechanics, as well as customize conformity of a 3D printed mesh. In comparison to existing meshes, the present meshes can reduce the incidence of chronic pain after implantation, as well as other complications. Additionally, modulating properties such as the microvoids or interstices between the nodes, the pore size distribution of the mesh, and the porosity can improve ingrowth of a patient's tissue and result in healthier tissue after surgery. In some embodiments, other mechanical responses of the mesh can be manipulated, e.g., tensile stiffness in different directions, tensile shear stiffness, and flexural stiffness. In additional embodiments, the geometry of the mesh, e.g., its 3D curvature and porosity, can also be manipulated. These mechanical responses can then be customized to fit the underlying tissue. Material composition can also be tuned throughout the implant to change properties including absorption by the patient. In some embodiments, the implant can include a non-absorbable filament such as polypropylene in some parts, which can provide long-term mechanical support, while other parts can include an absorbable polymer such as polylactic acid or polyglycolic acid for providing temporary support. The mechanical support provided by the implant can be spatially and temporally planned to maximize comfort and reinforcement while minimizing complications. In some embodiments, the mesh can be composed of different substances, e.g., conductive, elastic, high-strength, or drug eluting materials, to produce meshes with varying functionality.

By 3D printing, the part can also be customized through tailoring the geometry and mechanics using information found about a patient through computed tomography or ultrasound imaging. Such customization can be important for complex meshes used in operations such as repairing pelvic organ prolapse or stress urinary incontinence where complication rates are currently very high. In some embodiments, the mesh can include dense filament over the hole to be patched itself, while the remainder of the part can be much less dense and shaped such that it simply maintains the part covering the hole in place via hooks or similar attachment devices.

Further, if bacteria come into contact with the implanted mesh, they can attach themselves and multiply, forming a biofilm that protects from antibiotics. Existing mesh can also exacerbate recurrence, chronic pain, and infection. Surgical meshes are typically flat and have uniform mechanical stiffness, while the tissues they are intended to support feature great variation in curvature, stiffness, and direction of motion. This mismatch leads to stress concentrations and shear forces that cause mesh folding and displacement, while preventing the conversion of stiff scar tissue into tough, healthy tissue. Both extensive stitching and large mesh overlap around the site of operation are needed to keep the mesh in place, further damaging the tissue. Small pores magnify chronic pain/discomfort as scars will fuse into a large, palpable mass. Further, the uniform density of the mesh, even in areas that only provide overlap or an anchor, contributes to scar tissue formation and patient discomfort without providing useful support.

Continuous or pre-made fiber are understood in this application to refer to fibers that were not extruded during the 3D printing process used to make the device. The present disclosure provides for processes in which control of a 3D printer toolpath and hardware for patterning of continuous fibers can enable the additive manufacture of parts with locally controlled mechanics. More particularly, the present disclosure presents a hierarchical approach of designing and manufacturing a mesh in which elements with controlled geometry, connectivity, and/or composition can be combined into unit cells. This approach can enable the production of meshes in which non-linear tensile and flexural response, as well as other properties such as Poisson's ratio and sensing capability, can be locally programmed.

A non-limiting list of features and benefits of fabrics and devices that can be produced in view of the present disclosure can include a brace or other mechanical support device that can be 3D printed, either in whole or in part, and can include at least a portion of a mesh or fabric that can have one or more of the following characteristics: nonlinear mechanics that can be controlled by at least one of localized slack, fiber geometry, or material composition of the fabric or mesh; layers in which bonding can be controlled to enable compliance with a natural range of motion except in a direction or range of motion that the brace or mechanical support device is intended to curtail (e.g., ankle inversion); can be printed such that at least a portion of the mesh can exhibit a highly nonlinear stiffness, i.e., a modulus can be low at low strain and high at high strain; mesh can be integrated into a brace, garment, shoe, sock, glove, wearable, implantable, adhesive tape, athletic tape (which may or may not be adhesive), or other device; at least a portion of the mesh can contain one or more continuous fiber; and/or can include a mesh with at least a portion of the mesh printed on a curved surface where at least a portion of the mesh adheres to a substrate, and where the substrate can be removed at the end of the printing process and used as a component of a final device (e.g., brace, etc.). In some embodiments, unit cell and element designs in accordance with the present disclosure can be combined to create a mesh or portions of a mesh with a non-linear mechanical response that can match stress and strain values and/or profiles for a portion of human anatomy, e.g., muscle or connective tissue, and can be incorporated into a brace or other wearable device. Accordingly, mechanical support devices, such as braces, adhesive tapes, athletic tapes (which may or may not be adhesive), or other wearable devices, can be designed to address, among other things, soft tissue disorders by providing support to tissue or other portions of anatomy where needed without unnecessarily restricting a natural range of motion.

Examples of the above-described embodiments can include the following:

1. A wearable or implantable device, comprising:
    a mesh material configured to conform to a portion of an anatomy to serve as a support, the mesh material being made from one or more fibers and having a plurality of unit cells,
    wherein each unit cell of the plurality of unit cells includes at least one portion of fiber from the one or more fibers passing through the unit cell, and
    wherein the at least one portion of fiber that passes through the unit cell comprises at least one wave formed therein, the at least one wave being configured to influence a stiffness of the unit cell upon at least one of bending or stretching.
2. The wearable or implantable device of claim 1, wherein the at least one portion of fiber from the one or more fibers passing through the unit cell includes at least two portions of fiber from the one or more fibers passing through the unit cell, with a first portion of the at least two portions of fiber intersecting and being disposed at an angle with respect to a second portion of the at least two portions of fiber, and wherein at least one of the first portion or the second portion of the at least two portions of fiber that pass through the unit cell comprises the at least one wave formed therein.

3. The wearable or implantable device of claim 2, wherein the first portion of the at least two portions of fiber and the second portion of the at least two portions of fiber are comprised of different materials.

4. The wearable or implantable device of claim 2 or claim 3, wherein the first portion of the at least two portions of fiber is disposed substantially orthogonally with respect to the second portion of the at least two portions of fiber.

5. The wearable or implantable device of claim 4, wherein each unit cell of the plurality of unit cells includes the first portion of the at least two portions of fiber, the second portion of the at least two portions of fiber, a third portion of the at least two portions of fiber, and a fourth portion of the at least two portions of fiber, with the first and third portions being disposed substantially orthogonally with respect to the second and fourth portions.

6. The wearable or implantable device of claim 5, wherein the first, second, third, and fourth portions of fiber of the at least two portions of fiber are each from separate fibers, which are a first fiber, a second fiber, a third fiber, and a fourth fiber, respectively.

7. The wearable or implantable device of any of claims claim 2 to 6, wherein the first portion and the second portion of the at least two portions of fiber in some unit cells of the plurality of unit cells are selectively adhered together and the first portion and the second portion of the at least two portions of fiber in some other unit cells of the plurality of unit cells are selectively not adhered.

8. The wearable or implantable device of claim 7, wherein the first and second portions of the at least two portions of fibers that are selectively bonded together are non-stochastically and rationally distributed with respect to a volume of the mesh material.

9. The wearable or implantable device of any of claims 1 to 8,
wherein the device is a wearable device, and
wherein the mesh material being configured to conform to a portion of an anatomy to serve as a support serves as a mechanical support device.

10. The wearable device of claim 9, wherein the wearable device comprises one of: an ankle brace, a knee brace, a wrist brace, a back brace, or a neck brace.

11. The wearable device of claim 10, wherein the wearable device comprises the ankle brace, and the ankle brace is predominantly made from the mesh material.

12. The wearable device of claim 10, wherein the wearable device comprises the ankle brace, and the ankle brace is a pre-existing ankle brace, the mesh material being an additional material associated with the pre-existing ankle brace.

13. The wearable or implantable device of any of claims 1 to 8, wherein the device comprises a surgical mesh.

14. The wearable or implantable device of any of claims 1 to 8, wherein the device comprises a hernia mesh.

15. The wearable or implantable device of any of claims 1 to 8, wherein the device comprises an adhesive tape.

16. The wearable or implantable device of any one of claims 1 to 15, wherein the mesh material is non-woven.

17. The wearable or implantable device of any one of claims 1 to 16, wherein the mesh material is manufactured by extrusion of thermoplastic from one or more nozzles.

18. The wearable or implantable device of any one of claims 1 to 17, wherein the device is additively manufactured by extrusion of a mesh onto at least one of a: fabric, frame, support structure, or human.

19. The wearable or implantable device of claim 18, wherein the at least one of a: fabric, frame, support structure comprises at least one of the: fabric, frame, or support structure that is configured to be worn by a human.

20. The wearable or implantable device of claim 19, wherein the at least one of the: fabric, frame, or support structure is configured to be worn on a hand of the human.

21. The wearable or implantable device of any one of claims 1 to 20, wherein the one or more fibers comprises at least one continuous fiber that is continuous across multiple unit cells of the plurality of unit cells.

22. The wearable or implantable device of claim 21, wherein the at least one continuous fiber is continuous across multiple unit cells of the plurality of unit cells.

23. The wearable or implantable device of claim 21, wherein the at least one continuous fiber is continuous across an entire length of the mesh material.

24. The wearable or implantable device of claim 21, wherein the at least one continuous fiber is a single continuous fiber that makes up the entirety of the one or more fibers such that the one continuous fiber forms the mesh material.

25. The wearable or implantable device of any one of claims 1 to 24, wherein a region of the mesh material comprises localized slack.

26. The wearable or implantable device of any one of claims 1 to 25, wherein a region of the mesh material comprises a portion where a Poisson's ratio is negative, thereby allowing the mesh material to curve around a portion of an anatomy when stretched without folding.

27. The wearable or implantable device of any one of claims 1 to 26, wherein the mesh material further comprises a portion having a curvature formed therein, the mesh material having a non-linear tensile response at a location of the curvature.

28. The wearable or implantable device of any one of claims 1 to 27, wherein at least one fiber of the one or more fibers comprises a conductive thread configured to apply heat to a portion of an anatomy with which the mesh material is associated.

29. The wearable or implantable device of any one of claims 1 to 28, wherein at least one fiber of the one or more fibers comprises a conductive material configured to operate as a strain sensor.

30. The wearable or implantable device of any one of claims 1 to 29, wherein the mesh material has a highly non-linear stiffness such that a modulus is low under low strain conditions and the modulus is high under high strain conditions.

31. The wearable or implantable device of any one of claims 1 to 30, wherein at least one fiber of the one or more fibers comprises a pre-made fiber.

32. A wearable or implantable device, comprising:
- a first region having a plurality of first portions of extruded fiber disposed therein, the plurality of first portions of extruded fiber being configured to attach to a portion of human anatomy in a desired location; and
- a second region having a plurality of second portions of extruded fiber disposed therein, the plurality of second portions of extruded fiber being configured to conform to a portion of the human anatomy adjacent to the portion of the device attached to a portion of human anatomy in a desired location such that the plurality of second portions of extruded fiber permit substantially typical movement for the portion of the human anatomy they conform to unless that anatomy moves in a direction to an extent that would cause it to become injured,
- wherein at least one of local fabric geometry, topology, or composition of the extruded fiber controls whether portions of the extruded fiber are the plurality of first portions or the plurality of second portions of the extruded fiber.

33. The wearable or implantable device of claim 32, wherein the extruded fiber forms a mesh material.

34. The wearable or implantable device of claim 33, wherein the mesh material is non-woven.

35. The wearable or implantable device of claim 33 or claim 34, wherein the mesh material is manufactured by extrusion of thermoplastic from one or more nozzles.

36. The wearable or implantable device of any one of claims 32 to 35, wherein the extruded fiber comprises at least one continuous fiber that is continuous across multiple unit cells of the plurality of unit cells.

37. The wearable or implantable device of claim 36, wherein the at least one continuous fiber is continuous across an entire length of the mesh material.

38. The wearable or implantable device of claim 36, wherein the at least one continuous fiber is a single continuous fiber that makes up the entirety of the extruded fiber such that the one continuous fiber forms the mesh material.

39. The wearable or implantable device of any one of claims 33 to 38, wherein the mesh material further comprises a portion having a curvature formed therein, the mesh material having a non-linear tensile response at a location of the curvature.

40. The wearable or implantable device of any one of claims 33 to 39, wherein the mesh material has a highly non-linear stiffness such that a modulus is low under low strain conditions and the modulus is high under high strain conditions.

41. The wearable or implantable device of any one of claims 32 to 40, wherein the second region comprises localized slack.

42. The wearable or implantable device of claims 32 to 41, wherein the device is additively manufactured by extrusion of a mesh onto at least one of a: fabric, frame, support structure, adhesive tape, or human.

43. The wearable or implantable device of claim 42, wherein the at least one of the: fabric, frame, or support structure is configured to be worn by a human.

44. The wearable or implantable device of claim 43, wherein the at least one of the: fabric, frame, or support structure is configured to be worn on a hand of the human.

45. The wearable or implantable device of any of claims 32 to 44, wherein the device is a wearable device, the wearable device being a brace.

46. The wearable or implantable device of claim 45, wherein the brace comprises one of: an ankle brace, a knee brace, a wrist brace, a back brace, or a neck brace.

47. The wearable or implantable device of claim 46, wherein the wearable device comprises an ankle brace, and the ankle brace is predominantly made from the extruded fiber, the extruded fiber forming a mesh material.

48. The wearable or implantable device of any of claim 46, wherein the wearable device comprises an ankle brace, and the ankle brace is a pre-existing ankle brace, the extruded fiber being additional material associated with the pre-existing ankle brace.

49. The wearable or implantable device of any one of claims 32 to 42, wherein the device comprises a hernia mesh.

50. The wearable or implantable device of any one of claims 32 to 42, wherein the device comprises an adhesive tape.

51. The wearable or implantable device of any one of claims 32 to 50, wherein portions of the extruded fiber are selectively bonded together, and other portions of the extruded fiber are selectively unbonded.

52. The wearable or implantable device of claim 51, wherein the portions of the extruded fiber that are selectively bonded together are non-stochastically and rationally distributed with respect to a volume of the device.

53. The wearable or implantable device of any one of claims 32 to 52, wherein at least a portion of at least one of the first region or the second region has a Poisson's ratio that is negative, thereby allowing the portion of the at least one of the first region or the second region to curve around a portion of an anatomy when stretched without folding.

54. The wearable or implantable device of any one of claims 32 to 53, further comprising a conductive thread configured to apply heat to a portion of an anatomy with which the extruded fiber is associated.

55. The wearable or implantable device of any one of claims 32 to 54, wherein the extruded fiber comprises a conductive material configured to operate as a strain sensor.

56. The wearable or implantable device of any one of claims 32 to 55, wherein extruded fiber comprises a pre-made fiber.

57. A method for manufacturing a mesh material for a medical support, comprising:
- depositing a first portion of fiber onto a surface;
- depositing a second portion of fiber onto at least one of the first portion of fiber and the surface, the second portion including at least one wave formed therein to allow the second portion to bend with a lower stiffness before it stretches; and
- controlling at least one of local fabric geometry, topology, or composition of the deposited fiber to create portions that are configured to attach to a portion of human anatomy in a desired location and portions that are configured to conform to a portion of the human anatomy such that such portions permit substantially typical movement for a desired portion of the human anatomy unless that portion moves in a direction and to an extent that it would cause it to become injured.

58. The method of claim 57,
wherein the surface is an adhesive substrate, and
wherein at least one of depositing a first portion of fiber or depositing a second portion of fiber further comprises using the adhesive substrate to passively pull the respective first or second portion out of a nozzle and onto the adhesive substrate or the first portion of fiber.

59. The method of claim 58, further comprising depositing a third portion of fiber onto the adhesive substrate to change a direction in which the fiber is being printed.

60. The method of any of claims 57 to 59, wherein the surface comprises a first thermoplastic layer, and the method further comprises:
depositing a second thermoplastic layer on top of the first and second portions of fiber to sandwich the first and second portions of fiber between the first and second thermoplastic layers.

61. The method of any one of claims 57 to 60, wherein the medical support comprises a mechanical support device.

62. The method of claim 61, wherein the mechanical support device is configured to support one of: an ankle, a knee, a wrist, a back, or a neck.

63. The method of any one of claims 57 to 60, wherein the medical support comprises a hernia mesh.

64. The method of any one of claims 57 to 60, wherein the medical support comprises an adhesive tape.

65. The method of any one of claims 57 to 64, wherein the mesh material is non-woven.

66. The method of any one of claims 57 to 65, wherein the first portion of fiber and the second portion of fiber form at least one continuous fiber.

67. The method of claim 66, wherein the at least one continuous fiber is continuous across an entire length of the mesh material.

68. The method of claim 66, wherein the at least one continuous fiber is a single continuous fiber that forms the entirety of the mesh material.

69. The method of any one of claims 57 to 68, wherein depositing a second portion of fiber results in a region of the mesh material comprising localized slack.

70. The method of any one of claims 57 to 69, further comprising:
selectively binding together portions of the first portion of the fiber and portions of the second portion of the fiber; and
selectively leaving portions of the first portion of the fiber and portions of the second portion of the fiber unbonded.

71. The method of claim 70, wherein at least some of the portions of the first portion of the fiber and portions of the second portion of the fiber that are selectively bonded together are non-stochastically and rationally distributed with respect to a volume of the mesh material.

72. The method of any one of claims 57 to 71, further comprising forming a region of the mesh material in which a Poisson's ratio is negative, thereby allowing the mesh material to curve around a portion of an anatomy without folding.

73. The method of any one of claims 57 to 72, further comprising forming a portion of the mesh material to have a curvature formed therein, the mesh material having a non-linear tensile response at a location of the curvature.

74. The method of any one of claims 57 to 73, wherein the fiber comprises a pre-made fiber.

75. The method of any one of claims 57 to 61 or 65 to 74, wherein the fiber is attached to at least one of a: sock, shoe, adhesive tape, or other wearable product.

More broadly, the present disclosures are also by no means limited to medical implants. Any object involving fabric can be printed using the systems, devices, and methods provided for herein. A person skilled in the art could easily apply the present disclosures to manufacturing apparel, other types of medical implants, and in general most any object in which a fabric is used. Generally, the present disclosures are advantageous for any fabric because traditional fabrics that are woven or knitted have the same density across a surface area because otherwise it would typically unravel, while the present disclosures allows material to be deposited only where it is needed, so there is not necessarily a uniform density. Still further, these techniques can also be applied outside of objects having fabric, and can be more broadly applied to any 3D printing technique One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:
1. A wearable or implantable device, comprising:
a mesh material configured to conform to a portion of an anatomy to serve as a support, the mesh material being made from one or more fibers and having a plurality of unit cells,
wherein each unit cell of the plurality of unit cells includes at least one portion of fiber from the one or more fibers passing through the unit cell, and
wherein the at least one portion of fiber that passes through the unit cell comprises a plurality of waves formed therein, with each wave of the plurality of waves pointing in a common direction and being configured to influence a stiffness of the unit cell upon at least one of bending or stretching, and
wherein the one or more fibers are substantially linear between the plurality of waves.

2. The wearable or implantable device of claim 1,
wherein the at least one portion of fiber from the one or more fibers passing through the unit cell includes at least two portions of fiber from the one or more fibers passing through the unit cell, with a first portion of the at least two portions of fiber intersecting and being disposed at an angle with respect to a second portion of the at least two portions of fiber, and
wherein at least one of the first portion or the second portion of the at least two portions of fiber that pass through the unit cell comprises the plurality of waves formed therein.

3. The wearable or implantable device of claim 2, wherein the first portion and the second portion of the at least two portions of fiber in some unit cells of the plurality of unit cells are selectively adhered together and the first portion and the second portion of the at least two portions of fiber in some other unit cells of the plurality of unit cells are selectively not adhered.

4. The wearable or implantable device of claim 1,
wherein the device is a wearable device, and
wherein the mesh material being configured to conform to a portion of an anatomy to serve as a support serves as a mechanical support device.

5. The wearable or implantable device of claim 4, wherein the wearable device comprises one of: an ankle brace, a knee brace, a wrist brace, a back brace, or a neck brace.

6. The wearable or implantable device of claim 5, wherein the wearable device comprises the ankle brace, and the ankle brace is a pre-existing ankle brace, the mesh material being an additional material associated with the pre-existing ankle brace.

7. The wearable or implantable device of claim 1, wherein the device comprises a surgical mesh.

8. The wearable or implantable device of claim 1, wherein the device comprises an adhesive tape.

9. The wearable or implantable device of claim 1, wherein the one or more fibers comprises at least one continuous fiber that is continuous across multiple unit cells of the plurality of unit cells.

10. The wearable or implantable device of claim 1, wherein a region of the mesh material comprises localized slack.

11. The wearable or implantable device of claim 1, wherein the mesh material further comprises a portion having a curvature formed therein, the mesh material having a non-linear tensile response at a location of the curvature.

12. The wearable or implantable device of claim 1, wherein at least one fiber of the one or more fibers comprises a conductive material configured to operate as a strain sensor.

13. A wearable or implantable device, comprising:
a first region having a plurality of first portions of extruded fiber disposed therein, the plurality of first portions of extruded fiber being configured to attach to a portion of human anatomy in a desired location; and
a second region having a plurality of second portions of extruded fiber disposed therein, the plurality of second portions of extruded fiber being configured to conform to a portion of the human anatomy adjacent to the portion of the device attached to a portion of human anatomy in a desired location such that the plurality of second portions of extruded fiber permit substantially typical movement for the portion of the human anatomy they conform to unless that anatomy moves in a direction to an extent that would cause it to become injured,
wherein at least one of local fabric geometry, topology, or composition of the extruded fiber controls whether portions of the extruded fiber are the plurality of first portions or the plurality of second portions of the extruded fiber, and
wherein a plurality of first portions of extruded fiber or a plurality of second portions of extruded fiber comprise at least one wave formed therein, the plurality of first portions of extruded fiber or the plurality of second portions of extruded fiber being bonded such that the bonds are disposed separate from the at least one wave.

14. The wearable or implantable device of claim 13, wherein the extruded fiber forms a mesh material.

15. The wearable or implantable device of claim 14, wherein the mesh material has a plurality of unit cells, and the extruded fiber comprises at least one continuous fiber that is continuous across multiple unit cells of the plurality of unit cells.

16. The wearable or implantable device of claim 13, wherein the second region comprises localized slack.

17. The wearable or implantable device of claim 13, wherein the device is additively manufactured by extrusion of a mesh onto at least one of a: fabric, frame, support structure, adhesive tape, or human.

18. The wearable or implantable device of claim 13, wherein the wearable device comprises an ankle brace, and the ankle brace is predominantly made from the extruded fiber, the extruded fiber forming a mesh material.

19. The wearable or implantable device of claim 13, wherein the device comprises an adhesive tape in which an adhesive is coupled onto a mesh material.

20. The wearable or implantable device of claim 13, wherein portions of the extruded fiber are selectively bonded together, and other portions of the extruded fiber are selectively unbonded.

21. The wearable or implantable device of claim 13, wherein at least a portion of at least one of the first region or the second region has a Poisson's ratio that is negative, thereby allowing the portion of the at least one of the first region or the second region to curve around a portion of an anatomy when stretched without folding.

22. The wearable or implantable device of claim 1, wherein the unit cell comprising a plurality of waves is spaced from another unit cell comprising a plurality of waves by a unit cell that is devoid of a plurality of waves.

* * * * *